(12) United States Patent
Cuevas-Cordobés et al.

(10) Patent No.: US 10,035,805 B2
(45) Date of Patent: Jul. 31, 2018

(54) TRICYCLIC TRIAZOLIC COMPOUNDS

(71) Applicant: LABORATORIOS DEL DR. ESTEVE S.A., Barcelona (ES)

(72) Inventors: Félix Cuevas-Cordobés, Valdemoro (ES); Miguel Angel Pericás-Brondo, Espluges de Llobregat (ES)

(73) Assignee: ESTEVE PHARMACEUTECALS, S.A., Barcelona (ES)

( * ) Notice: Subject to any disclaimer, the term of this patent is extended or adjusted under 35 U.S.C. 154(b) by 0 days.

(21) Appl. No.: 15/323,228

(22) PCT Filed: Jul. 2, 2015

(86) PCT No.: PCT/EP2015/065063
§ 371 (c)(1),
(2) Date: Dec. 30, 2016

(87) PCT Pub. No.: WO2016/001345
PCT Pub. Date: Jan. 7, 2016

(65) Prior Publication Data
US 2017/0313710 A1    Nov. 2, 2017

(30) Foreign Application Priority Data
Jul. 2, 2014 (EP) .................................. 14382254

(51) Int. Cl.
*A61K 31/551* (2006.01)
*A61K 31/4985* (2006.01)
*C07D 487/14* (2006.01)

(52) U.S. Cl.
CPC .................. *C07D 487/14* (2013.01)

(58) Field of Classification Search
CPC . A61K 31/551; A61K 31/4985; C07D 487/14
USPC .......... 514/220, 250; 540/499, 558; 544/346
See application file for complete search history.

(56) References Cited

FOREIGN PATENT DOCUMENTS

WO    WO2009071657    6/2009

OTHER PUBLICATIONS

Snyder, Solomon. H., et al., "Receptor mechanisms in antipsychotic drug action: Focus on sigma receptors", Journal of Neuropsychiatry, 1988, pp. 7-15.

*Primary Examiner* — Brenda L Coleman
(74) *Attorney, Agent, or Firm* — Hueschen and Sage

(57) ABSTRACT

The present invention relates to new tricyclic triazolic compounds having a great affinity for sigma receptors, especially sigma-1 receptors, as well as to the process for the preparation thereof, to compositions comprising them, and to their use as medicaments.

17 Claims, No Drawings

TRICYCLIC TRIAZOLIC COMPOUNDS

FIELD OF THE INVENTION

The present invention relates to new tricyclic triazolic compounds having a great affinity for sigma receptors, especially sigma-1 receptors, as well as to the process for the preparation thereof, to compositions comprising them, and to their use as medicaments.

BACKGROUND OF THE INVENTION

The search for new therapeutic agents has been greatly aided in recent years by better understanding of the structure of proteins and other biomolecules associated with target diseases. One important class of these proteins are the sigma (σ) receptors, cell surface receptors of the central nervous system (CNS) which may be related to the dysphoric, hallucinogenic and cardiac stimulant effects of opioids. From studies of the biology and function of sigma receptors, evidence has been presented that sigma receptor ligands may be useful in the treatment of psychosis and movement disorders such as dystonia and tardive dyskinesia, and motor disturbances associated with Huntington's chorea or Tourette's syndrome and in Parkinson's disease (Walker, J. M. et al, Pharmacological Reviews, 1990, 42, 355). It has been reported that the known sigma receptor ligand rimcazole clinically shows effects in the treatment of psychosis (Snyder, S. H., Largent, B. L. J. Neuropsychiatry 1989, 1, 7). The sigma binding sites have preferential affinity for the dextrorotatory isomers of certain opiate benzomorphans, such as (+)-SKF 10047, (+)cyclazocine, and (+)-pentazocine and also for some narcoleptics such as haloperidol.

"The sigma receptor/s" as used in this application is/are well known and defined using the following citation: This binding site represents a typical protein different from opioid, NMDA, dopaminergic, and other known neurotransmitter or hormone receptor families (G. Ronsisvalle et al. Pure Appl. Chem. 73, 1499-1509 (2001)).

The sigma receptor has at least two subtypes, which may be discriminated by stereoselective isomers of these pharmacoactive drugs. SKF 10047 has nanomolar affinity for the sigma 1 (σ-1) site, and has micromolar affinity for the sigma 2 (σ-2) site. Haloperidol has similar affinities for both subtypes.

The Sigma-1 receptor is a non-opiaceous type receptor expressed in numerous adult mammal tissues (e.g. central nervous system, ovary, testicle, placenta, adrenal gland, spleen, liver, kidney, gastrointestinal tract) as well as in embryo development from its earliest stages, and is apparently involved in a large number of physiological functions. Its high affinity for various pharmaceuticals has been described, such as for SKF-10047, (+)-pentazocine, haloperidol and rimcazole, among others, known ligands with analgesic, anxiolytic, antidepressive, antiamnesic, antipsychotic and neuroprotective activity. Sigma-1 receptor is of great interest in pharmacology in view of its possible physiological role in processes related to analgesia, anxiety, addiction, amnesia, depression, schizophrenia, stress, neuroprotection and psychosis [Kaiser et al (1991) Neurotransmissions 7 (1): 1-5], [Walker, J. M. et al, Pharmacological Reviews, 1990, 42, 355] and [Bowen W. D. (2000) Pharmaceutica Acta Helvetiae 74: 211-218].

The Sigma-2 receptor is also expressed in numerous adult mammal tissues (e.g. nervous system, immune system, endocrine system, liver, kidney). Sigma-2 receptors can be components in a new apoptosis route that may play an important role in regulating cell proliferation or in cell development. This route seems to consist of Sigma-2 receptors joined to intracellular membranes, located in organelles storing calcium, such as the endoplasmic reticulum and mitochondria, which also have the ability to release calcium from these organelles. The calcium signals can be used in the signaling route for normal cells and/or in induction of apoptosis.

Agonists of Sigma-2 receptors induce changes in cell morphology, apoptosis in several types of cell lines and regulate the expression of p-glycoprotein mRNA, so that they are potentially useful as antineoplasic agents for treatment of cancer. In fact, Sigma-2 receptor agonists have been observed to induce apoptosis in mammary tumour cell lines resistant to common antineoplasic agents that damage DNA. In addition, agonists of Sigma-2 receptors enhance the cytotoxic effects of these antineoplasic agents at concentrations in which the agonist is not cytotoxic. Thus, agonists of Sigma-2 receptors can be used as antineoplasic agents at doses inducing apoptosis or at sub-toxic doses in combination with other antineoplasic agents to revert the resistance to the drug, thereby allowing using lower doses of the antineoplasic agent and considerably reducing its adverse effects.

Antagonists of Sigma-2 receptors can prevent the irreversible motor side effects caused by typical neuroleptic agents. In fact, it has been found that antagonists of Sigma-2 receptors can be useful as agents for improving the weakening effects of delayed dyskinesia appearing in patients due to chronic treatment of psychosis with typical antipsychotic drugs, such as haloperidol. Sigma-2 receptors also seem to play a role in certain degenerative disorders in which blocking these receptors could be useful.

Endogenous sigma ligands are not known, although progesterone has been suggested to be one of them. Possible sigma-site-mediated drug effects include modulation of glutamate receptor function, neurotransmitter response, neuroprotection, behavior, and cognition (Quirion, R. et al. Trends Pharmacol. Sci., 1992, 13:85-86). Most studies have implied that sigma binding sites (receptors) are plasmalemmal elements of the signal transduction cascade. Drugs reported to be selective sigma ligands have been evaluated as antipsychotics (Hanner, M. et al. Proc. Natl. Acad. Sci., 1996, 93:8072-8077). The existence of sigma receptors in the CNS, immune and endocrine systems have suggested a likelihood that it may serve as link between the three systems.

In view of the potential therapeutic applications of agonists or antagonists of the sigma receptor, a great effort has been directed to find selective ligands. Thus, the prior art discloses different sigma receptor ligands.

For instance, the international patent application WO2007/098961 describes 4,5,6,7 tetrahydrobenzo[b]thiophene derivatives having pharmacological activity towards the sigma receptor.

Spiro[benzopyran] or spiro[benzofuran] derivatives were also disclosed in EP1847542 as well as pyrazole derivatives (EP1634873) with pharmacological activity on sigma receptors.

WO2009/071657 discloses some tricyclic triazolic compounds although structurally different to the ones of the current invention with activity towards sigma receptors.

Nevertheless, there is still a need to find compounds having pharmacological activity towards the sigma receptor, being both effective and selective, and having good "drugability" properties, i.e. good pharmaceutical properties related to administration, distribution, metabolism and excretion.

Surprisingly, the authors of the present invention have observed that the new tricyclic triazolic compounds with general formula (I) show an affinity for Sigma receptor ranging from good to excellent. These compounds are therefore particularly suitable as pharmacologically active agents in medicaments for the prophylaxis and/or treatment of disorders or diseases related to Sigma receptors.

SUMMARY OF THE INVENTION

The present invention discloses novel compounds with great affinity to sigma receptors and having high solubility in a physiological media which might be used for the treatment of sigma related disorders or diseases.

Specifically, it is an object of the present invention novel tricyclic triazolic compounds of general formula (I):

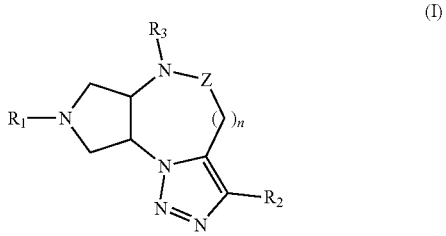

wherein $R_1$ is a H; a $C_{1-6}$ alkyl optionally substituted by at least one substitutent selected from a halogen, $C_{1-3}$-alkoxy, $C_{1-3}$-alkyl, $C_{1-3}$-haloalcoxy, $C_{1-3}$-haloalkyl, trihaloalkyl or a hydroxyl group; a $C_{3-9}$ cycloalkyl optionally substituted by at least one substitutent selected from a halogen, $C_{1-3}$-alkoxy, $C_{1-3}$-alkyl, $C_{1-3}$-haloalcoxy, $C_{1-3}$-haloalkyl, trihaloalkyl or a hydroxyl group; a 5 or 6-membered heterocycloalkyl having at least one heteroatom selected from O, N or S and being optionally substituted by at least one substitutent selected from a halogen, $C_{1-3}$-alkoxy, $C_{1-3}$-alkyl, $C_{1-3}$-haloalcoxy, $C_{1-3}$-haloalkyl, trihaloalkyl or a hydroxyl group; a 5 or 6-membered aryl optionally substituted by at least one substitutent selected from a halogen, $C_{1-3}$-alkoxy, $C_{1-3}$ alkyl, $C_{1-3}$-haloalcoxy, $C_{1-3}$-haloalkyl, trihaloalkyl or a hydroxyl group; a 5 or 6-membered heteroaryl having at least one heteroatom selected from O, N or S and being optionally substituted by at least one substitutent selected from a halogen, $C_{1-3}$-alkoxy, $C_{1-3}$-alkyl, $C_{1-3}$-haloalcoxy, $C_{1-3}$-haloalkyl, trihaloalkyl or a hydroxyl group; a —$(C(R_4)_2)_m$—$C_{3-9}$ cycloalkyl, the cycloalkyl group being optionally substituted by at least one substitutent selected from a halogen, $C_{1-3}$-alkoxy, $C_{1-3}$-alkyl, $C_{1-3}$-haloalcoxy, $C_{1-3}$-haloalkyl, trihaloalkyl or a hydroxyl group; a —$(C(R_4)_2)_m$-heterocycloalkyl, the heterocycloalkyl group being a 5 or 6-membered ring having at least one heteroatom selected from O, N or S and being optionally substituted by at least one substitutent selected from a halogen, $C_{1-3}$-alkoxy, $C_{1-3}$-alkyl, $C_{1-3}$-haloalcoxy, $C_{1-3}$-haloalkyl, trihaloalkyl or a hydroxyl group; a —$(C(R_4)_2)_m$-aryl, the aryl group being a 5 or 6-membered ring optionally substituted by at least one substituent selected from a halogen, $C_{1-3}$-alkoxy, $C_{1-3}$-alkyl, $C_{1-3}$-haloalcoxy, $C_{1-3}$-haloalkyl, trihaloalkyl or a hydroxyl group; or a —$(C(R_4)_2)_m$-heteroaryl, the heteroaryl group being a 5 or 6-membered ring having at least one heteroatom selected from O, N or S and being optionally substituted by at least one substitutent selected from a halogen, $C_{1-3}$-alkoxy, $C_{1-3}$-alkyl, $C_{1-3}$-haloalcoxy, $C_{1-3}$-haloalkyl, trihaloalkyl or a hydroxyl group;

$R_2$ is a 5 or 6-membered aryl optionally substituted by at least one substitutent selected from a halogen, $C_{1-3}$-alkoxy, $C_{1-3}$-alkyl, $C_{1-3}$-haloalcoxy, $C_{1-3}$-haloalkyl, trihaloalkyl or a hydroxyl group; or a substituted 5 or 6-membered heteroaryl optionally substituted by at least one substitutent selected from a halogen, $C_{1-3}$-alkoxy, $C_{1-3}$-alkyl, $C_{1-3}$-haloalcoxy, $C_{1-3}$-haloalkyl, trihaloalkyl or a hydroxyl group;

$R_3$ is a H; a $C_{1-6}$ alkyl optionally substituted by at least one substitutent selected from a halogen, $C_{1-3}$-alkoxy, $C_{1-3}$-alkyl, $C_{1-3}$-haloalcoxy, $C_{1-3}$-haloalkyl, trihaloalkyl or a hydroxyl group; —$(C(R_4)_2)_m$—$C_{3-9}$ cycloalkyl optionally substituted by at least one substitutent selected from a halogen, $C_{1-3}$-alkoxy, $C_{1-3}$-alkyl, $C_{1-3}$-haloalcoxy, $C_{1-3}$-haloalkyl, trihaloalkyl or a hydroxyl group; a —$SO_2R_5$ group; a —$COR_6$ group; a —$CO_2R_7$ group; or a —$(C(R_4)_2)_m$—$CONR_8R_9$;

$R_4$ is H or a $C_{1-6}$ alkyl;

$R_5$, $R_6$ and $R_7$ are a $C_{1-6}$ alkyl optionally substituted by at least one substitutent selected from a halogen, $C_{1-3}$-alkoxy, $C_{1-3}$-alkyl, $C_{1-3}$-haloalcoxy, $C_{1-3}$-haloalkyl, trihaloalkyl or a hydroxyl group;

$R_8$ and $R_9$ independently represent a H, a $C_{1-6}$ alkyl; or a —$(C(R_4)_2)_m$-aryl, the aryl group being a 5 or 6-membered ring optionally substituted by at least one substitutent selected from a 5 or 6-membered heterocycloalkyl, a halogen, $C_{1-3}$-alkoxy, $C_{1-3}$-alkyl, $C_{1-3}$-haloalcoxy, $C_{1-3}$-haloalkyl, trihaloalkyl or a hydroxyl group;

Z is $CH_2$ or C=O and n is 0 or 1 m is 0, 1 or 2;

or a pharmaceutically acceptable salt, isomer, prodrug or solvate thereof.

It is also an object of the invention different processes for the preparation of compounds of formula (I).

Another object of the invention refers to the use of such compounds of general formula I for the treatment or prophylaxis of sigma receptor mediated diseases or conditions, especially sigma-1 mediated diseases or conditions. Within the group of diseases or conditions mediated by sigma receptor for which the compounds of the invention are effective diarrhea, lipoprotein disorders, hyperlipidemia, hypertriglyceridemia, hypercholesterolemia, obesity, migraine, arthritis, hypertension, arrhythmia, ulcer, glaucoma, learning, memory and attention deficits, cognition disorders, neurodegenerative diseases, demyelinating diseases, addiction to drugs and chemical substances including cocaine, amphetamine, ethanol and nicotine; tardive diskinesia, ischemic stroke, epilepsy, stroke, stress, cancer, psychotic conditions, in particular depression, anxiety or schizophrenia; inflammation or autoimmune diseases, may be cited. Compounds of the invention are especially useful in the treatment and prophylaxis of pain, especially neuropathic pain, inflammatory pain or other pain conditions involving allodynia and/or hyperalgesia.

It is also an object of the invention pharmaceutical compositions comprising one or more compounds of general formula (I) with at least one pharmaceutically acceptable excipient. The pharmaceutical compositions in accordance with the invention can be adapted in order to be administered by any route of administration, be it orally or parenterally, such as pulmonarily, nasally, rectally and/or intravenously. Therefore, the formulation in accordance with the invention may be adapted for topical or systemic application, particu-

DETAILED DESCRIPTION OF THE INVENTION

The invention first relates to compounds of general formula (I)

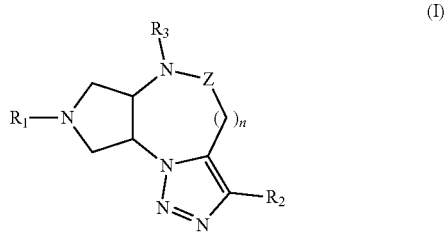

wherein
R$_1$ is a H; a C$_{1-6}$ alkyl optionally substituted by at least one substitutent selected from a halogen, C$_{1-3}$-alkoxy, C$_{1-3}$-alkyl, C$_{1-3}$-haloalcoxy, C$_{1-3}$-haloalkyl, trihaloalkyl or a hydroxyl group; a C$_{3-9}$ cycloalkyl optionally substituted by at least one substitutent selected from a halogen, C$_{1-3}$-alkoxy, C$_{1-3}$-alkyl, C$_{1-3}$-haloalcoxy, C$_{1-3}$-haloalkyl, trihaloalkyl or a hydroxyl group; a 5 or 6-membered heterocycloalkyl having at least one heteroatom selected from O, N or S and being optionally substituted by at least one substitutent selected from a halogen, C$_{1-3}$-alkoxy, C$_{1-3}$-alkyl, C$_{1-3}$-haloalcoxy, C$_{1-3}$-haloalkyl, trihaloalkyl or a hydroxyl group; a 5 or 6-membered aryl optionally substituted by at least one substitutent selected from a halogen, C$_{1-3}$-alkoxy, C$_{1-3}$ alkyl, C$_{1-3}$-haloalcoxy, C$_{1-3}$-haloalkyl, trihaloalkyl or a hydroxyl group; a 5 or 6-membered heteroaryl having at least one heteroatom selected from O, N or S and being optionally substituted by at least one substitutent selected from a halogen, C$_{1-3}$-alkoxy, C$_{1-3}$-alkyl, C$_{1-3}$-haloalcoxy, C$_{1-3}$-haloalkyl, trihaloalkyl or a hydroxyl group; a —(C(R$_4$)$_2$)$_m$—C$_{3-9}$ cycloalkyl, the cycloalkyl group being optionally substituted by at least one substitutent selected from a halogen, C$_{1-3}$-alkoxy, C$_{1-3}$-alkyl, C$_{1-3}$-haloalcoxy, C$_{1-3}$-haloalkyl, trihaloalkyl or a hydroxyl group; a —(C(R$_4$)$_2$)$_m$-heterocycloalkyl, the heterocycloalkyl group being a 5 or 6-membered ring having at least one heteroatom selected from O, N or S and being optionally substituted by at least one substitutent selected from a halogen, C$_{1-3}$-alkoxy, C$_{1-3}$-alkyl, C$_{1-3}$-haloalcoxy, C$_{1-3}$-haloalkyl, trihaloalkyl or a hydroxyl group; a —(C(R$_4$)$_2$)$_m$-aryl, the aryl group being a 5 or 6-membered ring optionally substituted by at least one substitutent selected from a halogen, C$_{1-3}$-alkoxy, C$_{1-3}$-alkyl, C$_{1-3}$-haloalcoxy, C$_{1-3}$-haloalkyl, trihaloalkyl or a hydroxyl group; or a —(C(R$_3$)$_2$)$_m$-heteroaryl, the heteroaryl group being a 5 or 6-membered ring having at least one heteroatom selected from O, N or S and being optionally substituted by at least one substitutent selected from a halogen, C$_{1-3}$-alkoxy, C$_{1-3}$-alkyl, C$_{1-3}$-haloalcoxy, C$_{1-3}$-haloalkyl, trihaloalkyl or a hydroxyl group;
R$_2$ is a 5 or 6-membered aryl optionally substituted by at least one substitutent selected from a halogen, C$_{1-3}$-alkoxy, C$_{1-3}$-alkyl, C$_{1-3}$-haloalcoxy, C$_{1-3}$-haloalkyl, trihaloalkyl or a hydroxyl group; or a substituted 5 or 6-membered heteroaryl optionally substituted by at least one substitutent selected from a halogen, C$_{1-3}$-alkoxy, C$_{1-3}$-alkyl, C$_{1-3}$-haloalcoxy, C$_{1-3}$-haloalkyl, trihaloalkyl or a hydroxyl group;
R$_3$ is a H; a C$_{1-6}$ alkyl optionally substituted by at least one substitutent selected from a halogen, C$_{1-3}$-alkoxy, C$_{1-3}$-alkyl, C$_{1-3}$-haloalcoxy, C$_{1-3}$-haloalkyl, trihaloalkyl or a hydroxyl group; —(C(R$_4$)$_2$)$_m$—C$_{3-9}$ cycloalkyl optionally substituted by at least one substitutent selected from a halogen, C$_{1-3}$-alkoxy, C$_{1-3}$-alkyl, C$_{1-3}$-haloalcoxy, C$_{1-3}$-haloalkyl, trihaloalkyl or a hydroxyl group; a —SO$_2$R$_5$ group; a —COR$_6$ group; a —CO$_2$R$_7$ group; or a —(C(R$_4$)$_2$)$_m$—CONR$_8$R$_9$;
R$_4$ is H or a C$_{1-6}$ alkyl;
R$_5$, R$_6$ and R$_7$ are a C$_{1-6}$ alkyl optionally substituted by at least one substitutent selected from a halogen, C$_{1-3}$-alkoxy, C$_{1-3}$-alkyl, C$_{1-3}$-haloalcoxy, C$_{1-3}$-haloalkyl, trihaloalkyl or a hydroxyl group;
R$_8$ and R$_9$ independently represent a H, a C$_{1-6}$ alkyl; or a —(C(R$_4$)$_2$)$_m$-aryl, the aryl group being a 5 or 6-membered ring optionally substituted by at least one substitutent selected from a 5 or 6-membered heterocycloalkyl, a halogen, C$_{1-3}$-alkoxy, C$_{1-3}$-alkyl, C$_{1-3}$-haloalcoxy, C$_{1-3}$-haloalkyl, trihaloalkyl or a hydroxyl group;
Z is CH$_2$ or C═O and
n is 0 or 1;
m is 0, 1 or 2;
or a pharmaceutically acceptable salt, isomer, prodrug or solvate thereof.

Unless otherwise stated, the compounds of the invention are also meant to include isotopically-labelled forms i.e. compounds which differ only in the presence of one or more isotopically-enriched atoms. For example, compounds having the present structures except for the replacement of at least one hydrogen atom by a deuterium or tritium, or the replacement of at least one carbon by $^{13}$C- or $^{14}$C-enriched carbon, or the replacement of at least one nitrogen by $^{15}$N-enriched nitrogen are within the scope of this invention.

The compounds of formula (I) or their salts or solvates are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I), or of its salts, solvates or prodrugs.

One preferred pharmaceutically acceptable form is the crystalline form, including such form in pharmaceutical composition. In the case of salts and solvates the additional ionic and solvent moieties must also be non-toxic. The compounds of the invention may present different polymorphic forms, it is intended that the invention encompasses all such forms.

"Halogen" or "halo" as referred in the present invention represent fluorine, chlorine, bromine or iodine.

"C$_{1-6}$ alkyl", as referred to in the present invention, are saturated aliphatic radicals. They may be linear or branched and are optionally substituted. C$_{1-6}$alkyl as expressed in the present invention means an alkyl radical of 1, 2, 3, 4, 5 or 6 carbon atoms. Preferred alkyl radicals according to the present invention include but are not restricted to methyl, ethyl, propyl, n-propyl, isopropyl, butyl, n-butyl, tert-butyl, isobutyl, sec-butyl, 1-methylpropyl, 2-methylpropyl, 1,1-dimethylethyl, pentyl, n-pentyl, 1,1-dimethylpropyl, 1,2-dimethylpropyl, 2,2-dimethylpropyl, hexyl, 1-methylpentyl. Alkyl radicals, as defined in the present invention, are optionally mono- or polysubstituted by substitutents independently selected from a halogen, $C_{1-3}$-alkoxy, $C_{1-3}$-alkyl, $C_{1-3}$-haloalcoxy, $C_{1-3}$-haloalkyl, trihaloalkyl or a hydroxyl group "$C_{3-9}$ Cycloalkyl" as referred to in the present invention, is understood as meaning saturated and unsaturated (but not aromatic), cyclic hydrocarbons having from 3 to 9 carbon atoms which can optionally be unsubstituted, mono- or polysubstituted. Examples for cycloalkyl radical preferably include but are not restricted to cyclopropyl, 2-methylcyclopropyl, cyclopropylmethyl, cyclobutyl, cyclopentyl, cyclopentylmethyl, cyclohexyl, cycloheptyl, cyclooctyl, adamantyl, noradamantyl. Cycloalkyl radicals, as defined in the present invention, are optionally mono- or polysubstituted by substitutents independently selected from a halogen, $C_{1-3}$-alkyl, $C_{1-3}$-alkoxy, $C_{1-3}$-haloalcoxy, $C_{1-3}$-haloalkyl, trihaloalkyl or a hydroxyl group.

"Heterocycloalkyl" as referred to in the present invention, are understood as meaning saturated and unsaturated (but not aromatic), cyclic hydrocarbons which can optionally be unsubstituted, mono- or polysubstituted and which have at least one heteroatom in their structure selected from N, O or S. Examples for heterocycloalkyl radical preferably include but are not restricted to pyrroline, pyrrolidine, pyrazoline, aziridine, azetidine, tetrahydropyrrole, oxirane, oxetane, dioxetane, tetrahydropyrane, tetrahydrofurane, dioxane, dioxolane, oxazolidine, piperidine, piperazine, morpholine, azepane or diazepane. Heterocycloalkyl radicals, as defined in the present invention, are optionally mono- or polysubstituted by substitutents independently selected from a halogen, $C_{1-3}$-alkyl, $C_{1-3}$-alkoxy, $C_{1-3}$-haloalcoxy, $C_{1-3}$-haloalkyl, trihaloalkyl or a hydroxyl group. More preferably heterocycloalkyl in the context of the present invention are 5 or 6-membered ring systems optionally at least monosubstituted.

"Aryl" as referred to in the present invention, is understood as meaning ring systems with at least one aromatic ring but without heteroatoms even in only one of the rings. These aryl radicals may optionally be mono- or polysubstituted by substitutents independently selected from a halogen, $C_{1-3}$-alkoxy, $C_{1-3}$-haloalcoxy, $C_{1-3}$-haloalkyl or a hydroxyl group. Preferred examples of aryl radicals include but are not restricted to phenyl, naphthyl, fluoranthenyl, fluorenyl, tetralinyl, indanyl or anthracenyl radicals, which may optionally be mono- or polysubstituted, if not defined otherwise. More preferably aryl in the context of the present invention are 5 or 6-membered ring systems optionally at least monosubstituted.

"Heteroaryl" as referred to in the present invention, is understood as meaning heterocyclic ring systems which have at least one aromatic ring and may optionally contain one or more heteroatoms from the group consisting of nitrogen or oxygen and may optionally be mono- or polysubstituted by substitutents independently selected from a halogen, $C_{1-3}$-alkyl, $C_{1-3}$-alkoxy, $C_{1-3}$-haloalcoxy, $C_{1-3}$-haloalkyl trihaloalkyl or a hydroxyl group. Preferred examples of heteroaryls include but are not restricted to furan, benzofuran, pyrrole, pyridine, pyrimidine, pyridazine, pyrazine, quinoline, isoquinoline, phthalazine, triazole, pyrazole, isoxazole, indole, benzotriazole, benzodioxolane, benzodioxane, benzimidazole, carbazole and quinazoline. More preferably heteroaryl in the context of the present invention are 5 or 6-membered ring systems optionally at least monosubstituted.

The term "condensed" according to the present invention means that a ring or ring-system is attached to another ring or ring-system, whereby the terms "annulated" or "annelated" are also used by those skilled in the art to designate this kind of attachment.

The term "ring system" according to the present invention refers to ring systems comprising saturated, unsaturated or aromatic carbocyclic ring systems which contain optionally at least one heteroatom as ring member and which are optionally at least mono-substituted. Said ring systems may be condensed to other carbocyclic ring systems such as aryl groups, naphtyl groups, heteroaryl groups, cycloalkyl groups, etc.

The term "salt" is to be understood as meaning any form of the active compound according to the invention in which this assumes an ionic form or is charged and is coupled with a counter-ion (a cation or anion) or is in solution. By this are also to be understood complexes of the active compound with other molecules and ions, in particular complexes which are complexed via ionic interactions. The definition particularly includes physiologically acceptable salts, this term must be understood as equivalent to "pharmacologically acceptable salts".

The term "pharmaceutically acceptable salts" in the context of this invention means any salt that is tolerated physiologically (normally meaning that it is not toxic, particularly as a result of the counter-ion) when used in an appropriate manner for a treatment, particularly applied or used in humans and/or mammals. These physiologically acceptable salts may be formed with cations or bases and, in the context of this invention, are understood to be salts formed by at least one compound used in accordance with the invention—normally an acid (deprotonated)—such as an anion and at least one physiologically tolerated cation, preferably inorganic, particularly when used on humans and/or mammals. Salts with alkali and alkali earth metals are particularly preferred, as well as those formed with ammonium cations ($NH_4^+$). Preferred salts are those formed with (mono) or (di)sodium, (mono) or (di)potassium, magnesium or calcium. These physiologically acceptable salts may also be formed with anions or acids and, in the context of this invention, are understood as being salts formed by at least one compound used in accordance with the invention—normally protonated, for example in nitrogen—such as a cation and at least one physiologically tolerated anion, particularly when used on humans and/or mammals. This definition specifically includes in the context of this invention a salt formed by a physiologically tolerated acid, i.e. salts of a specific active compound with physiologically tolerated organic or inorganic acids—particularly when used on humans and/or mammals. Examples of this type of salts are those formed with: hydrochloric acid, hydrobromic acid, sulphuric acid, methanesulfonic acid, formic acid, acetic acid, oxalic acid, succinic acid, malic acid, tartaric acid, mandelic acid, fumaric acid, lactic acid or citric acid.

The term "solvate" is to be understood as meaning any form of the active compound according to the invention in which this compound has attached to it via non-covalent binding another molecule (most likely a polar solvent) especially including hydrates and alcoholates, e.g. methanolate.

The term "prodrug" is used in its broadest sense and encompasses those derivatives that are converted in vivo to the compounds of the invention. Such derivatives would readily occur to those skilled in the art, and include, depending on the functional groups present in the molecule and without limitation, the following derivatives of the compounds of the invention: esters, amino acid esters, phosphate esters, metal salts sulfonate esters, carbamates, and amides. Examples of well known methods of producing a prodrug of a given acting compound are known to those skilled in the art and can be found e.g. in Krogsgaard-Larsen et al. "Textbook of Drug design and Discovery" Taylor & Francis (april 2002).

Any compound that is a prodrug of a compound of formula (I) is within the scope of the invention. Particularly favored prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

In a particular and preferred embodiment of the invention $R_1$ is a H; a $C_{1-6}$ alkyl optionally substituted by at least one substitutent selected from a halogen, $C_{1-3}$-alkoxy, $C_{1-3}$-alkyl, $C_{1-3}$-haloalcoxy, $C_{1-3}$-haloalkyl, trihaloalkyl or a hydroxyl group; a 5 or 6-membered heterocycloalkyl having at least one heteroatom selected from O, N or S and being optionally substituted by at least one substitutent selected from a halogen, $C_{1-3}$-alkoxy, $C_{1-3}$-alkyl, $C_{1-3}$-haloalcoxy, $C_{1-3}$-haloalkyl, trihaloalkyl or a hydroxyl group; a —$(C(R_4)_2)_m$—$C_{3-9}$ cycloalkyl, the cycloalkyl group being optionally substituted by at least one substitutent selected from a halogen, $C_{1-3}$-alkoxy, $C_{1-3}$-alkyl, $C_{1-3}$-haloalcoxy, $C_{1-3}$-haloalkyl, trihaloalkyl or a hydroxyl group; or a —$(C(R_4)_2)_m$-aryl, the aryl group being a 5 or 6-membered ring optionally substituted by at least one substitutent selected from a halogen, $C_{1-3}$-alkoxy, $C_{1-3}$-alkyl, $C_{1-3}$-haloalcoxy, $C_{1-3}$-haloalkyl, trihaloalkyl or a hydroxyl group where $R_4$ and m are as expressed above for formula (I).

In a still more particular and preferred embodiment $R_1$ is H, a $C_{1-6}$ alkyl or a group selected from:

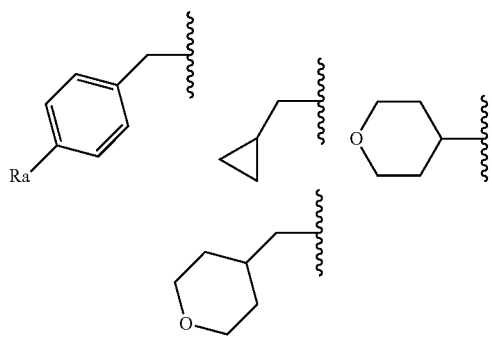

wherein $R_a$ represents a hydrogen, a halogen, $C_{1-3}$ alkyl, or a trihaloalkyl.

In another particular embodiment of the invention, $R_2$ is a phenyl optionally substituted by at least one halogen atom.

In still another particular embodiment of the invention $R_3$ is a H; a $C_{1-6}$ alkyl; —$(C(R_4)_2)_m$—$C_{3-9}$ cycloalkyl; a —$SO_2R_5$ group; a —$COR_6$ group; or a —$CO_2R_7$ group; wherein $R_4$ and m are as defined in claim 1 and $R_5$, $R_6$ and $R_7$ are $C_{1-6}$ alkyl.

The more preferred embodiment of the invention is that of compounds of general formula I wherein $R_1$ is H, a $C_{1-6}$ alkyl or a group selected from:

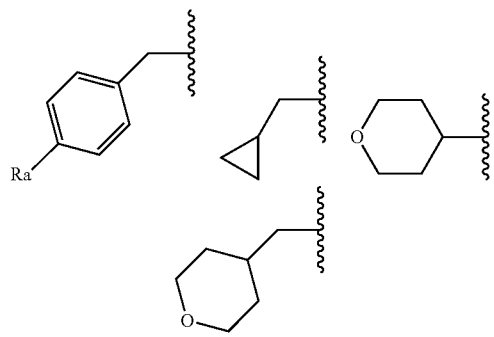

wherein $R_a$ represents a hydrogen, a halogen, $C_{1-3}$ alkyl, or a trihaloalkyl;

$R_2$ is a phenyl optionally substituted by at least one halogen atom; and $R_3$ is a H; a $C_{1-6}$ alkyl; —$(C(R_4)_2)_m$—$C_{3-9}$ cycloalkyl; a —$SO_2R_5$ group; a —$COR_6$ group; or a —$CO_2R_7$ group; wherein $R_4$ and m are as expressed above for formula (I) and $R_5$, $R_6$ and $R_7$ are $C_{1-6}$ alkyl.

A specific embodiment of the invention is that in which the tricyclic triazolic compounds of the invention represent a compound with the general formula (Ia):

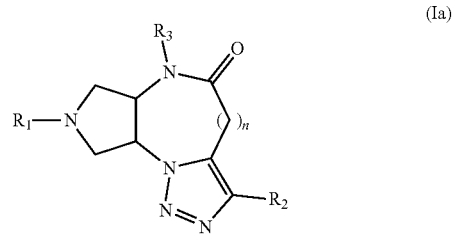

wherein $R_1$, $R_2$, $R_3$ and n have the same meaning as defined above for compounds of formula (I).

or a pharmaceutically acceptable salt, isomer, prodrug or solvate thereof.

A further specific embodiment of the invention is that in which the tricyclic triazolic compounds of the invention represent a compound with the general formula (Ib):

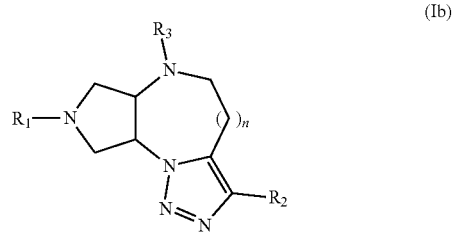

wherein $R_1$, $R_2$, $R_3$ and n have the same meaning as defined above for compounds of formula (I).

or a pharmaceutically acceptable salt, isomer, prodrug or solvate thereof.

Another specific embodiment of the invention is that in which the tricyclic triazolic compounds of the invention represent a compound with the general formula (Ic):

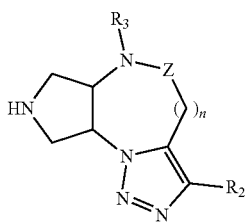

wherein $R_2$, $R_3$, Z and n have the same meaning as defined above for compounds of formula (I).

Another specific embodiment of the invention is that in which the tricyclic triazolic compounds of the invention represent a compound with the general formula (Id):

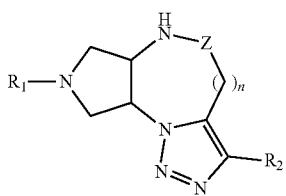

wherein $R_1$, $R_3$, Z and n have the same meaning as defined above for compounds of formula (I).

The compounds of the present invention represented by the above described formula (I) may include enantiomers depending on the presence of chiral centers or isomers depending on the presence of double bonds (e.g. Z, E). The single isomers, enantiomers or diastereoisomers and mixtures thereof fall within the scope of the present invention.

In particular, compounds referred to herein may have asymmetric centers and therefore exist in different enantiomeric or diastereomeric forms accordingly to the following general formulas:

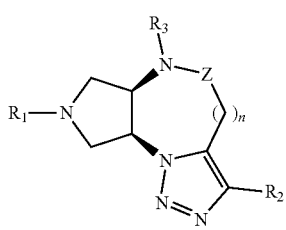

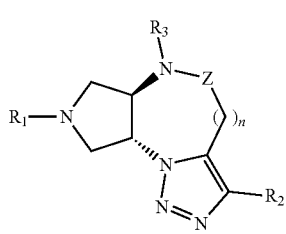

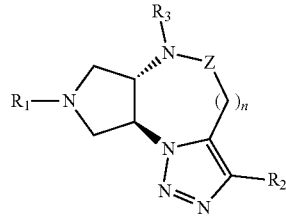

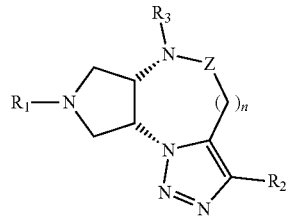

wherein $R_1$, $R_2$, $R_3$, Z and n have the above defined meaning.

Among all the compounds described in the general formula (I), particularly preferred are any of those compounds selected from:

(rac) (5a,8a-trans)-7-benzyl-3-phenyl-5,5a,6,7,8,8a-hexahydro-4H-pyrrolo[3,4-e][1,2,3]triazolo[1,5-a]pyrazine, hydrochloride, (rac)-(5a,8a-cis)-7-benzyl-3-phenyl-5,5a,6,7,8,8a-hexahydro-4H-pyrrolo[3,4-e][1,2,3]triazolo[1,5-a]pyrazin-4-one, (rac) (5a,8a-cis)-7-benzyl-3-phenyl-5,5a,6,7,8,8a-hexahydro-4H-pyrrolo[3,4-e][1,2,3]triazolo[1,5-a]pyrazine, (rac) 1-((5a,8a-trans)-7-benzyl-3-phenyl-6,7,8,8a-tetrahydro-4H-pyrrolo[3,4-e][1,2,3]triazolo[1,5-a]pyrazin-5(5aH)-yl)ethanone hydrochloride, (rac)-(5a,8a-cis)-7-benzyl-3-phenyl-5-propyl-5,5a,6,7,8,8a-hexahydro-4H-pyrrolo[3,4-e][1,2,3]triazolo[1,5-a]pyrazin-4-one, (rac)-(5a,8a-trans)-tert-butyl-3-phenyl-6,7,8,8a-tetrahydro-4H-pyrrolo[3,4-e][1,2,3]triazolo[1,5-a]pyrazine-5(5aH)-carboxylate, (rac)-(5a,8a-trans)-tert-butyl-7-(4-fluorobenzyl)-3-phenyl-6,7,8,8a-tetrahydro-4H-pyrrolo[3,4-e][1,2,3]triazolo[1,5-a]pyrazine-5(5aH)-carboxylate, (rac) (5a,8a-trans)-7-(4-fluorobenzyl)-3-phenyl-5,5a,6,7,8,8a-hexahydro-4H-pyrrolo[3,4-e][1,2,3]triazolo[1,5-a]pyrazine hydrochloride, (rac) (5a,8a-trans)-7-benzyl-3-phenyl-5-propyl-5,5a,6,7,8,8a-hexahydro-4H-pyrrolo[3,4-e][1,2,3]triazolo[1,5-a]pyrazine hydrochloride, (rac) (5a,8a-trans)-3-phenyl-5-propyl-5,5a,6,7,8,8a-hexahydro-4H-pyrrolo[3,4-e][1,2,3]triazolo[1,5-a]pyrazine hydrochloride, (rac) (5a,8a-trans)-7-pentyl-3-phenyl-5-propyl-5,5a,6,7,8,8a-hexahydro-4H-pyrrolo[3,4-e][1,2,3]triazolo[1,5-a]pyrazine hydrochloride, (rac) (5a,8a-cis)-7-benzyl-5-methyl-3-phenyl-5,5a,6,7,8,8a-hexahydro-4H-pyrrolo[3,4-e][1,2,3]triazolo[1,5-a]pyrazine, (rac) (5a,8a-cis)-7-benzyl-3-phenyl-5-propyl-5,5a,6,7,8,8a-hexahydro-4H-pyrrolo[3,4-e][1,2,3]triazolo[1,5-a]pyrazine, (rac) (5a,8a-cis)-7-pentyl-3-phenyl-5,5a,6,7,8,8a-hexahydro-4H-pyrrolo[3,4-e][1,2,3]triazolo[1,5-a]pyrazine, (5aS,8aR)-7-benzyl-3-phenyl-5,5a,6,7,8,8a-hexahydro-4H-pyrrolo[3,4-e][1,2,3]triazolo[1,5-a]pyrazine, (rac) (5a,8a-trans)-7-benzyl-5-methyl-3-phenyl-5,5a,6,7,8,8a-hexahydro-4H-pyrrolo[3,4-e][1,2,3]triazolo[1,5-a]pyrazine hydrochloride, (rac) 1-((5a,8a-trans)-7-benzyl-3-phenyl-6,7,8,8a-tetrahydro-4H-pyrrolo[3,4-e][1,2,3]triazolo[1,5-a]pyrazin-5(5aH)-yl)propan-1-one hydrochloride, (rac) (5a,8a-trans)-7-(cyclopropyl-methyl)-3-phenyl-5,5a,6,7,8,8a-hexahydro-4H-pyrrolo[3,4-e][1,2,3]triazolo[1,5-a]pyrazine hydrochloride, (rac) (5a,8a-trans)-3-phenyl-7-(tetrahydro-2H-pyran-4-yl)-5,5a,6,7,8,8a-hexahydro-4H-pyrrolo[3,4-e][1,2,3]triazolo[1,5-a]pyrazine hydrochloride, (rac) (5a,8a-trans)-7-benzyl-5-(methylsulfonyl)-3-phenyl-5,5a,6,7,8,8a-hexahydro-4H-pyrrolo[3,4-e][1,2,3]triazolo[1,5-a]pyrazine hydrochloride, (5aS,8aS)-7-benzyl-3-phenyl-5,5a,6,7,8,8a-hexahydro-4H-pyrrolo[3,4-e][1,2,3]triazolo[1,5-a]pyrazine hydrochloride, (5aR,8aR)-7-benzyl-3-phenyl-5,5a,6,7,8,8a-hexahydro-4H-pyrrolo[3,4-e][1,2,3]triazolo[1,5-a]pyrazine hydrochloride, (5aS,8aS)-7-(4-fluorobenzyl)-3-phenyl-5,5a,6,7,8,8a-hexahydro-4H-pyrrolo[3,4-e][1,2,3]triazolo[1,5-a]pyrazine hydrochloride, (5aR,8aR)-7-(4-fluorobenzyl)-3-phenyl-5,5a,6,7,8,8a-hexahydro-4H-pyrrolo[3,4-e][1,2,3]triazolo[1,5-a]pyrazine hydrochloride, (5aR,8aR)-7-(4-chlorobenzyl)-3-phenyl-5,5a,6,7,8,8a-hexahydro-4H-pyrrolo[3,4-e][1,2,3]triazolo[1,5-a]pyrazine hydrochloride, (5aR,8aR)-3-phenyl-7-(4-(trifluoromethyl)benzyl)-5,5a,6,7,8,8a-hexahydro-4H-pyrrolo[3,4-e][1,2,3]triazolo[1,5-a]pyrazine hydrochloride, (5aR,8aR)-3-phenyl-7-((tetrahydro-2H-pyran-4-yl)methyl)-5,5a,6,7,8,8a-hexahydro-4H-pyrrolo[3,4-e][1,2,3]triazolo[1,5-a]pyrazine hydrochloride, (rac) (5a,8a-trans)-7-benzyl-3-(2-fluorophenyl)-5,5a,6,7,8,8a-hexahydro-4H-pyrrolo[3,4-e][1,2,3]triazolo[1,5-a]pyrazine hydrochloride, (5aR,8aR)-7-benzyl-3-(2-fluorophenyl)-5,5a,6,7,8,8a-hexahydro-4H-pyrrolo[3,4-e][1,2,3]triazolo[1,5-a]pyrazine hydrochloride, (rac) (6a,9a-cis)-8-benzyl-3-phenyl-4,5,6,6a,7,8,9,9a-octahydropyrrolo[3,4-b][1,2,3]triazolo[1,5-d][1,4]diazepine hydrochloride, (rac) (6a,9a-cis)-8-benzyl-3-phenyl-6-propyl-4,5,6,6a,7,8,9,9a-octahydropyrrolo[3,4-b][1,2,3]triazolo[1,5-d][1,4]diazepine hydrochloride, (rac) (6a,9a-cis)-8-benzyl-6-(cyclopropylmethyl)-3-phenyl-4,5,6,6a,7,8,9,9a-octahydropyrrolo[3,4-b][1,2,3]triazolo[1,5-d][1,4]diazepine hydrochloride, (rac) 1-((6a,9a-cis)-8-benzyl-3-phenyl-4,5,7,8,9,9a-hexahydropyrrolo[3,4-b][1,2,3]triazolo[1,5-d][1,4]diazepin-6(6aH)-yl)propan-1-one hydrochloride, (6aR,9aS)-8-benzyl-3-phenyl-4,5,6,6a,7,8,9,9a-octahydropyrrolo[3,4-b][1,2,3]triazolo[1,5-d][1,4]diazepine hydrochloride, (6aS,9aR)-8-benzyl-3-phenyl-4,5,6,6a,7,8,9,9a-octahydropyrrolo[3,4-b][1,2,3]triazolo[1,5-d][1,4]-diazepine hydrochloride, (rac)-(5a,8a-cis)-3-phenyl-5,5a,6,7,8,8a-hexahydro-4H-pyrrolo[3,4-e][1,2,3]triazolo[1,5-a]pyrazin-4-one hydrochloride and (rac)-(5a,8a-cis)-7-benzyl-5-methyl-3-phenyl-5,5a,6,7,8,8a-hexahydro-4H-pyrrolo[3,4-e][1,2,3]triazolo[1,5-a]pyrazin-4-one.

In another aspect, the invention refers to the processes for obtaining the compounds of general formula (I). Several procedures have been developed for obtaining all the compounds of the invention, and the procedures will be explained below in methods A, B and C.

The obtained reaction products may, if desired, be purified by conventional methods, such as crystallization and chromatography. Where the processes described below for the preparation of compounds of the invention give rise to mixtures of stereoisomers, these isomers may be separated by conventional techniques such as preparative chromatography. If there are chiral centers the compounds may be prepared in racemic form, or individual enantiomers may be prepared either by enantiospecific synthesis or by resolution.

Method A

Method A represents a first process for synthesizing compounds according to general formula (I). Method A allows for the preparation of compounds of general formula (Ia) and (Ib) that is compounds of formula (I) where Z represents either a —$CH_2$— or a C=O.

In this sense, a process is presented for the preparation of a compound of general formula (I):

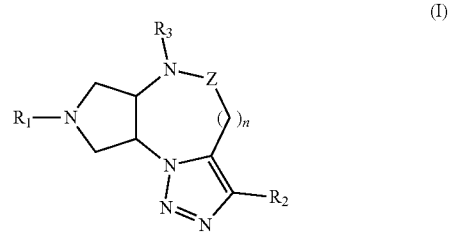

(I)

comprising the cycloaddition reaction of a compound of general formula (II) or its enantiomers:

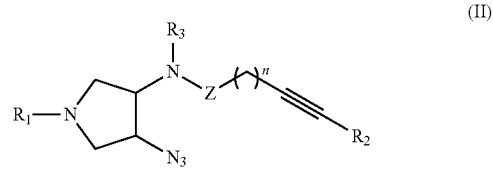

(II)

wherein $R_1$, $R_2$, $R_3$, Z and n are as above for general formula (I).

The cycloaddition reaction of compound (II) is preferably carried out in an apolar solvent such as, for instance, xylene or toluene. The temperature used in the reaction is preferably in the range from room temperature to reflux.

Scheme 1 is a representation of the cycloaddition reaction for the case where Z represents a —$CH_2$— or C=O giving rise to compounds (Ia) and (Ib) respectively.

Scheme 1

(Ib)

(II)

(Ia)

As represented in scheme 1 compounds of general formula (Ib) can also be obtained by reduction of compounds of general formula (Ia). This reduction reaction is preferably carried out in an aprotic solvent such as tetrahydrofuran (THF) in the presence of a reducing agent such as LiAlH$_4$ or BH$_3$ at a temperature ranging from room temperature to solvent reflux temperature Method B Method B represents an alternative way to method A for preparing compounds of general formula (I).

In this sense, a process is described for the preparation of a compound of general formula (I):

(I)

comprising the reaction in an organic solvent of a compound of general formula (Ic):

(Ic)

with a compound of general formula (IIIa) or (VIa):

(IIIa)

(VIa)

wherein R$_1$, R$_2$, R$_3$, Z and n are as defined above for formula (I) and X is a suitable leaving group, such as a halogen or sulfonate.

When compound (Ic) is reacted with (IIIa) the reaction is preferably carried out in the presence of a base such as diisopropylethylamine (DIPEA), triethylamine or NaH, in an organic solvent such as dichloromethane (DCM), THF or DMF.

On the alternative the reaction of compound (Ic) with a carbonyl derivative (VIa) is carried out in the presence of a reduction agent such as NaBH(OAc)$_3$, in a organic solvent such as dichloroethane (DCE). In some cases additionally the reaction can be carried out in the presence of a base such as DIPEA or TEA, or alternatively in the presence of an acid, preferably acetic acid. The type of carbonyl derivative of formula (VIa) to be used will depend on the meaning of the final substituent R$_1$ desired. For instance, if R$_1$ is intended to represent a methyl group, formaldehyde should be used in the reaction, if an ethyl group is desired in the position R$_1$ acetaldehyde should be used etc.

Compounds of formula (I) where R$_1$ is a benzyl (Bn) can be converted to compounds of formula (Ic) (R$_1$=H). This conversion can be accomplished by reaction of compounds of formula (I) with ammonium formate in the presence of a catalyst such as Pd in carbon and in a polar solvent, such as methanol. The reaction temperature should be between 20° C. to 75° C. Alternatively, deprotection can be done by hydrogenation with hydrogen also preferably in the presence of a catalyst such as Pd in carbon and in a polar solvent, such as methanol. The reaction can also be done in the additional presence of an acid preferably HCl.

The reactions of method B are represented in scheme 2

Scheme 2

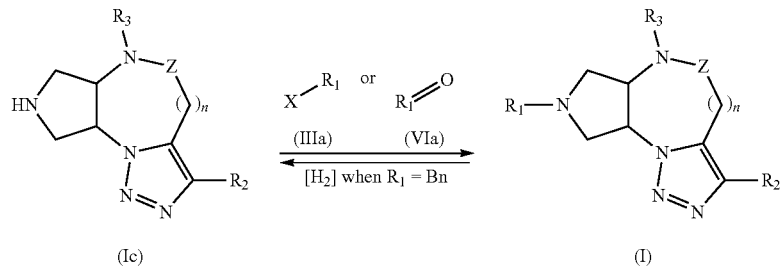

(Ic)    (I)

Method C

Method C represents an additional process for synthesizing compounds according to general formula (I).

In this sense, a process is described for the preparation of a compound of general formula (I):

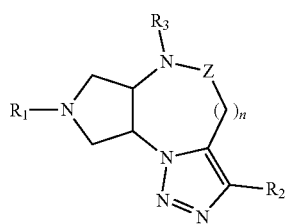

(I)

comprising the reaction in an organic solvent of a compound of general formula (Id):

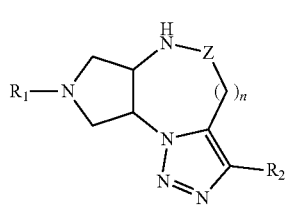

(Id)

with a compound of general formula (IIIb), (IV), (V) or (VIb):

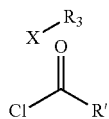

(IIIb)
(IV)

-continued (V)

(VIb)

wherein $R_1$, $R_2$, $R_3$, Z and n are as defined above for formula (I), R' stands for $R_5$ or $R_6$ as defined above for formula (I) and X is a suitable leaving group, such as a halogen or sulfonate.

When compound (Id) is reacted with (IIIb), (IV) or (V) the reaction is preferably carried out in the presence of a base such as diisopropylethylamine (DIPEA), triethylamine (TEA) or NaH, in an organic solvent such as dichloromethane (DCM), THF or DMF.

On the alternative the reaction of compound (Id) with an carbonyl derivative (VIb) is carried out in the presence of a reduction agent such as $NaBH(OAc)_3$, in a organic solvent such as dichloroethane (DCE). In some cases additionally the reaction can be carried out in the presence of a base such as DIPEA or TEA, or alternatively in the presence of an acid, preferably acetic acid. The type of carbonyl derivative of formula (VIb) to be used will depend on the meaning of the final substituent $R_3$ desired. For instance, if $R_3$ is intended to represent a methyl group, formaldehyde should be used in the reaction, if an ethyl group is desired in the position $R_3$ acetaldehyde should be used etc.

Compounds of formula (I) where $R_3$ is a tertbutoxycarbonyl (Boc) can be converted to compounds of formula (Id) ($R_3$=H) by reaction with an acid preferably HCl or trifluoroacetic acid.

The reactions of method C are represented in scheme 3:

Scheme 3

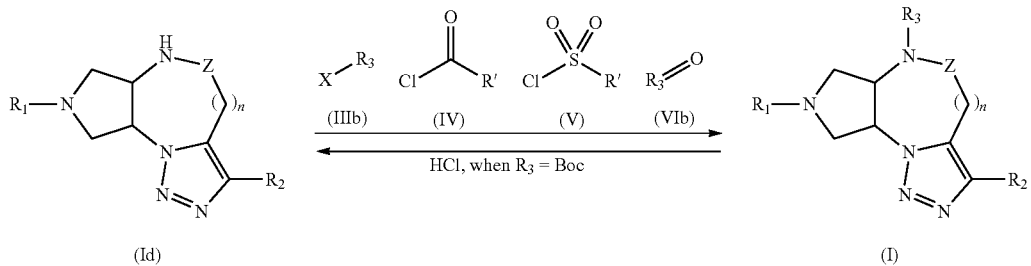

(Id)    (I)

Compounds of formula (II), (IIIa), (IIIb), (IV), (V), (VIa), (VIb) as shown above or compounds (VII), (VIII), (IX), (X), (XI), (XII), (XIII), (XIV) and (XV) mentioned below are commercially available or may be prepared by routine reactions to a skilled person.

In particular, compound of general formula (II) can be prepared in two different ways depending on whether Z is —CH$_2$— or C=O.

In this sense, compounds of general formula (II) encompass compounds of general formula (IIa) and (IIb):

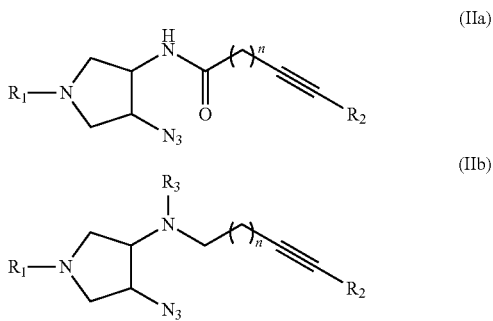

where R$_1$, R$_2$, R$_3$ and n have the meaning as defined above for formula (I).

Scheme 4a below represents the reaction for preparing compounds of formula (IIa) or its enantiomers. As observed compound (IIa) can be prepared by the reaction of a compound of formula (VII) or its enantiomers with a carboxylic acid (VIII) in the presence of a coupling activating agent, preferably N-(3-dimethylaminopropyl)-N'-ethylcarbodiimide hydrochloride (EDC), a coupling additive, preferably 1-hydroxybenzotriazole (HOBt) and in the presence of a base, preferably DIPEA or TEA. The reaction takes place in an organic solvent, such as DCM.

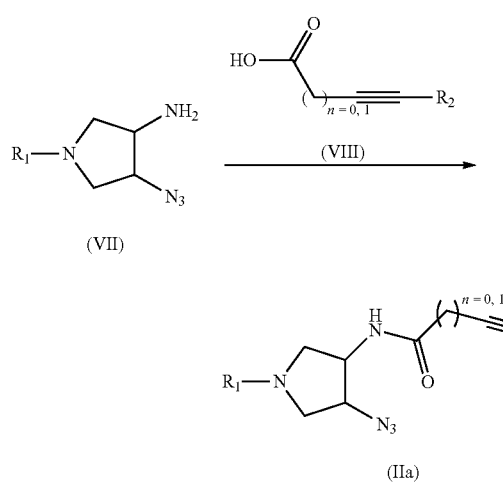

Compounds of general formula (IIb) can be prepared as represented below in scheme 4b by the reaction of an alcohol of formula (IX) or its enantiomers with diphenylphosporylazide, diisopropylazadicarboxylate and triphenylphosphine in an organic solvent, preferably THF, at a temperature range of 0° C. to 50° C. As an alternative, compounds of formula (IIb) can be prepared by reaction of a compound of formula (X) or its enantiomers with a compound of formula (XI), where X is a suitable leaving group as halogen or sulfonate, in the presence of a base, preferably NaH. The reaction is carried out in an organic solvent, such as DMF or THF, at a temperature range of room temperature to solvent reflux temperature.

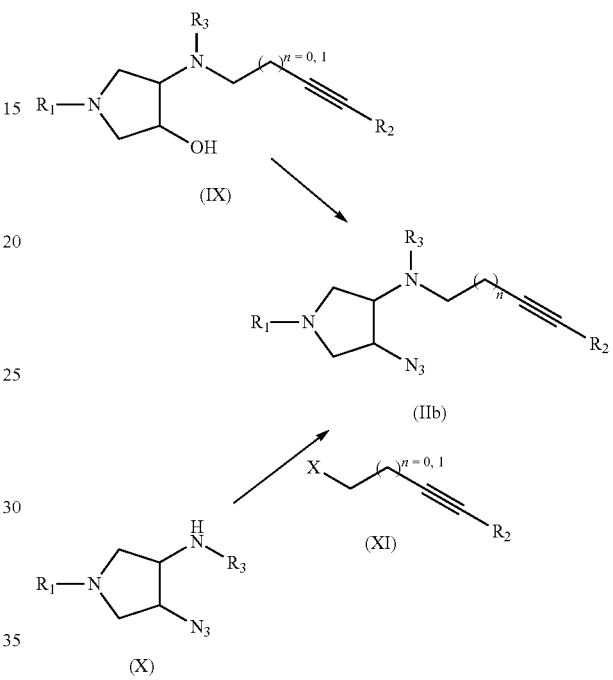

Intermediates of general formula (IX) or its enantiomers where R$_1$, R$_2$, R$_3$ and n have the meanings as defined above, can be prepared in several ways as described in scheme 5 below.

A compound of formula (IX) can be prepared by the reaction of an epoxide of formula (XII) with an amine (XIII), preferably in the presence of a catalyst, such as LiClO$_4$, in a polar solvent, such as acetonitrile (ACN), at a temperature range of room temperature to solvent reflux temperature.

Alternatively, intermediates of general formula (IX) or its enantiomers can be prepared by reaction of an aminoalcohol of formula (XIV) or its enantiomers with a compound of formula (XI), where X is a suitable leaving group, such as halogen or sulfonate, in the presence of a base, preferably K$_2$CO$_3$. The reaction is carried out in a polar solvent, such as ACN, at a temperature range of room temperature to solvent reflux temperature.

In a further alternative, compounds of formula (IX) can be prepared by reaction with an aldehyde (XV), in the presence of a reduction agent, preferably NaBH(OAc)$_3$. The reaction is carried out in an organic solvent, preferably DCE and in some cases, additionally in the presence of a base, such as DIPEA or TEA. The reaction between (IX) and (XV) can alternatively be carried out in the presence of NaBH$_4$ in a polar solvent, preferably MeOH, at a temperature range of room temperature to solvent reflux temperature.

Scheme 5

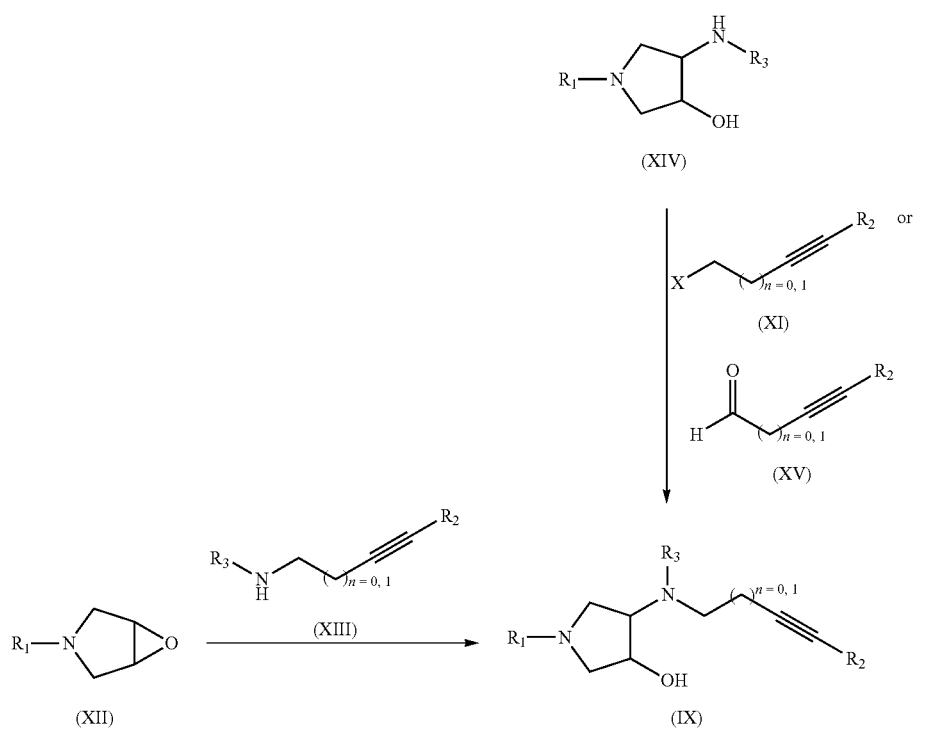

Compounds of general formula (IX) with cis stereochemistry or its enantiomers, where $R_1$, $R_2$ and have the meanings as defined above, can be prepared as described in scheme 6. The reaction consecutively comprises the steps of:

a) The reaction of a compound of formula IXa-trans or its enantiomers with tert-butoxycarbonyl anhydride in the presence of a base, preferably TEA, in an organic solvent, preferably DCM, at a temperature range of room temperature to solvent reflux temperature.

b) The reaction of a compound of formula IXb-trans or its enantiomers with methanesulfonyl chloride, in the presence of a base, preferably TEA, in an organic solvent, preferably DCM, at a temperature range of room temperature to solvent reflux temperature.

c) The hydrolysis of a compound of formula XVI-cis or its enantiomers with a base, preferably NaOH, in a mixture of organic solvent and water, preferably a mixture of MeOH and water, at a temperature range of room temperature to solvent reflux temperature.

Scheme 6

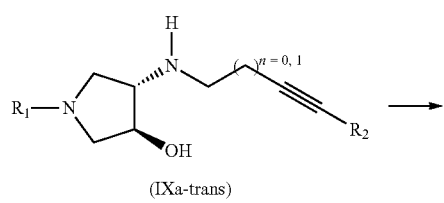

(IXa-trans)

-continued

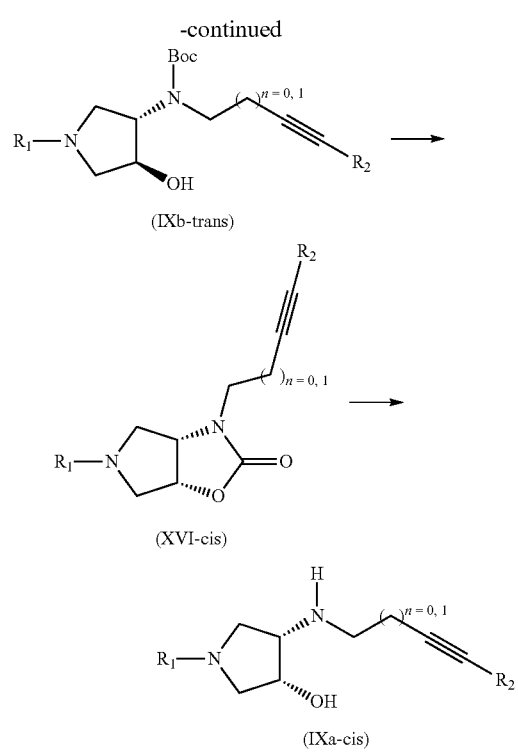

An additional aspect of the invention relates to the therapeutic use of the compounds of general formula (I). As mentioned above, compounds of general formula (I) show a strong affinity to sigma receptors and can behave as agonists, antagonists, inverse agonists, partial antagonists or partial agonists thereof. Therefore, compounds of general formula (I) are useful as medicaments.

They are suitable for the treatment and the prophylaxis of disorders and diseases mediated by sigma receptors, especially, sigma-1 receptors. In this sense, compounds of formula (I) are very good anxiolitic and immunosuppressant and are very useful in the treatment and prophylaxis of diarrhoea, lipoprotein disorders, hyperlipidemia, hypertriglyceridemia, hypercholesterolemia, obesity, migraine, arthritis, hypertension, arrhythmia, ulcer, glaucoma, learning, memory and attention deficits, cognition disorders, neurodegenerative diseases, demyelinating diseases, addiction to drugs and chemical substances including cocaine, amphetamine, ethanol and nicotine; tardive diskinesia, ischemic stroke, epilepsy, stroke, stress, cancer, psychotic conditions, in particular depression, anxiety or schizophrenia; inflammation or autoimmune diseases.

The compounds of formula (I) are especially suited for the treatment of pain, especially neuropathic pain, inflammatory pain or other pain conditions involving allodynia and/or hyperalgesia. PAIN is defined by the International Association for the Study of Pain (IASP) as "an unpleasant sensory and emotional experience associated with actual or potential tissue damage, or described in terms of such damage (IASP, Classification of chronic pain, 2nd Edition, IASP Press (2002), 210). Even though pain is always subjective its causes or syndromes can be classified.

In a preferred embodiment compounds of the invention are used for the treatment and prophylaxis of allodynia and more specifically mechanical or thermal allodynia.

In another preferred embodiment compounds of the invention are used for the treatment and prophylaxis of hyperalgesia.

In yet another preferred embodiment compounds of the invention are used for the treatment and prophylaxis of neuropathic pain and more specifically for the treatment and prophylaxis of hyperpathia.

A related aspect of the invention refers to the use of compounds of formula (I) for the manufacture of a medicament for the treatment or prophylaxis of disorders and diseases mediated by sigma receptors, as explained before.

Another related aspect of the invention refers to a method for the treatment or propylaxis of disorders and diseases mediated by sigma receptors, as explained before comprising the administration of a therapeutically effective amount of a compound of general formula (I) to a subject in need thereof.

Another aspect of the invention is a pharmaceutical composition which comprises at least a compound of general formula (I) or a pharmaceutically acceptable salt, prodrug, isomer or solvate thereof, and at least a pharmaceutically acceptable carrier, additive, adjuvant or vehicle.

The pharmaceutical composition of the invention can be formulated as a medicament in different pharmaceutical forms comprising at least a compound binding to the sigma receptor and optionally at least one further active substance and/or optionally at least one auxiliary substance.

The auxiliary substances or additives can be selected among carriers, excipients, support materials, lubricants, fillers, solvents, diluents, colorants, flavour conditioners such as sugars, antioxidants and/or agglutinants. In the case of suppositories, this may imply waxes or fatty acid esters or preservatives, emulsifiers and/or carriers for parenteral application. The selection of these auxiliary materials and/or additives and the amounts to be used will depend on the form of application of the pharmaceutical composition.

The pharmaceutical composition in accordance with the invention can be adapted to any form of administration, be it orally or parenterally, for example pulmonarily, nasally, rectally and/or intravenously.

Preferably, the composition is suitable for oral or parenteral administration, more preferably for oral, intravenous, intraperitoneal, intramuscular, subcutaneous, intrathekal, rectal, transdermal, transmucosal or nasal administration.

The composition of the invention can be formulated for oral administration in any form preferably selected from the group consisting of tablets, dragées, capsules, pills, chewing gums, powders, drops, gels, juices, syrups, solutions and suspensions.

The composition of the present invention for oral administration may also be in the form of multiparticulates, preferably microparticles, microtablets, pellets or granules, optionally compressed into a tablet, filled into a capsule or suspended in a suitable liquid. Suitable liquids are known to those skilled in the art.

Suitable preparations for parenteral applications are solutions, suspensions, reconstitutable dry preparations or sprays.

The compounds of the invention can be formulated as deposits in dissolved form or in patches, for percutaneous application.

Skin applications include ointments, gels, creams, lotions, suspensions or emulsions.

The preferred form of rectal application is by means of suppositories.

The respective medicament may—depending on its route of administration—also contain one or more auxiliary substances known to those skilled in the art. The medicament according to the present invention may be produced according to standard procedures known to those skilled in the art.

The daily dosage for humans and animals may vary depending on factors that have their basis in the respective species or other factors, such as age, sex, weight or degree of illness and so forth. The daily dosage for humans may preferably be in the range from 1 to 2000, preferably 1 to 1500, more preferably 1 to 1000 milligrams of active substance to be administered during one or several intakes per day.

The following examples are merely illustrative of certain embodiments of the invention and cannot be considered as restricting it in any way.

EXAMPLES

Examples of Preparation of Compounds of Formula (II)

Synthesis of (rac)-N-((3,4-cis)-4-azido-1-benzylpyrrolidin-3-yl)-3-phenylpropiolamide

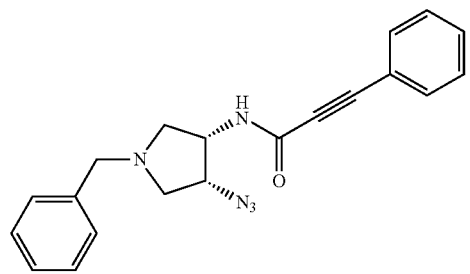 [SMILES: [N-]=[N+]=N[C@@H]1CN(Cc2ccccc2)C[C@@H]1NC(=O)C#Cc1ccccc1]

A mixture of phenylpropiolic acid (2.6 g, 18 mmol), N-(3-dimethylaminopropyl)-N'-ethylcarbodiimide hydrochloride (3.4 g, 18 mmol) and 1-hydroxybenzotriazole (2.4 g, 18 mmol) in DCM (80 mL) was stirred at r.t. for 1.5 h and then cooled at 0° C. A solution of (rac)-(3,4-cis)-4-azido-1-benzylpyrrolidin-3-amine (3.2 g, 14.8 mmol) and DIPEA (7.8 mL, 44.4 mmol) in DCM (80 mL) was added at 0° C. and the reaction mixture was allowed to warm to r.t. and stirred for 20 h. The reaction mixture was washed with NaHCO$_3$ aqueous saturated solution and then with water, dried over Na$_2$SO$_4$, filtered and concentrated. Purification by flash chromatography, silica gel, gradient hexane to hexane:ethyl acetate (7:3), afforded the title compound (2.75 g, 54% yield).

$^1$H-NMR (400 MHz, CDCl$_3$) δ ppm: 7.57 (m, 2H), 7.46-7.28 (m, 8H), 6.42 (d, J=8 Hz, 1H), 4.69 (m, 1H), 4.20 (m, 1H), 3.67 (s, 2H), 2.93 (m, 2H), 2.79 (dd, J$_1$=3.2 Hz, J$_2$=10.7 Hz, 1H), 2.59 (dd, J$_1$=6.1 Hz, J$_2$=9.8 Hz, 1H).

Synthesis of (rac)-(3,4-cis)-4-azido-1-benzyl-N-(3-phenyl prop-2-yn-1-yl)pyrrolidin-3-amine

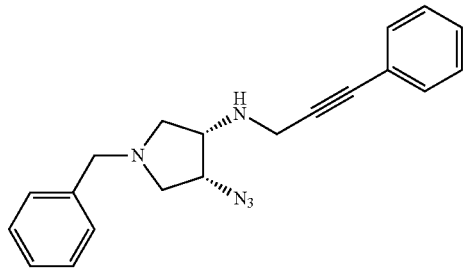 [SMILES: [N-]=[N+]=N[C@@H]1CN(Cc2ccccc2)C[C@@H]1NCC#Cc1ccccc1]

To a solution of triphenylphosphine (343 mg, 1.3 mmol) in dry THF (10 mL) under nitrogen atmosphere at 0° C., a solution of (rac)-(3,4-trans)-1-benzyl-4-((3-phenylprop-2-yn-1-yl)amino)pyrrolidin-3-ol (250 mg, 0.82 mmol) in THF (5 mL), diisopropyl-azodicarboxylate (0.25 mL, 1.3 mmol) and diphenylphosphorylazide (0.28 mL, 1.3 mmol) were added. The reaction mixture was stirred at r.t. for 20 h and then concentrated. Purification by flash chromatography, silica gel, gradient hexane to 30% ethyl acetate, afforded the title compound (190 mg, 70% yield).

$^1$H-NMR (400 MHz, CDCl$_3$) δ ppm: 7.40 (m, 2H), 7.31 (m, 8H), 4.10 (m, 1H), 3.70 (s, 2H), 3.69 (d, J=3.2 Hz, 2H), 3.61 (m, 1H), 3.11 (dd, J$_1$=5.7 Hz, J$_2$=10.5 Hz, 1H), 3.05 (dd, J$_1$=7.2 Hz, J$_2$=9.3 Hz, 1H), 2.74 (dd, J$_1$=3.6 Hz, J$_2$=10.5 Hz, 1H), 2.48 (dd, J$_1$=7.7 Hz, J$_2$=9.3 Hz, 1H).

Synthesis of (rac)-tert-butyl ((3,4-trans)-4-azido-1-benzylpyrrolidin-3-yl)(3-phenyl-prop-2-yn-1-yl) carbamate

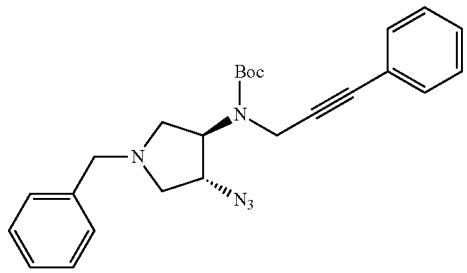 [SMILES: CC(C)(C)OC(=O)N(CC#Cc1ccccc1)[C@@H]1CN(Cc2ccccc2)C[C@H]1N=[N+]=[N-]]

To a suspension of NaH (15 mg, 0.37 mmol, 60% in mineral oil) in DMF (3 mL) cooled at 0° C., a solution of (rac)-tert-butyl((3,4-trans)-4-azido-1-benzylpyrrolidin-3-yl) carbamate (80 mg, 0.25 mmol) in DMF (3 mL) was added and the reaction mixture was stirred for 30 min. (3-Bromoprop-1-yn-1-yl)benzene (64 mg, 0.328 mmol) was added dropwise at 0° C. and the reaction mixture was allowed to warm to r.t. and stirred for 20 h. Purification by flash chromatography, silica gel, gradient hexane to 100% ethyl acetate to afford the title compound (56 mg, 51% yield).

$^1$H-NMR (400 MHz, CDCl$_3$) δ ppm: 7.34 (m, 10H), 4.49 (m, 1H), 4.40 (m, 1H), 4.25 (m, 2H), 3.64 (AB system, 2H), 3.10 (m, 1H), 2.86 (d, J=6.7 Hz, 2H), 2.48 (dd, J$_1$=5.7 Hz, J$_2$=9.8 Hz, 1H), 1.52 (s, 9H).

Alternatively: To a solution of (rac)-(3,4-trans)-4-azido-1-benzyl-N-(3-phenylprop-2-yn-1-yl)pyrrolidin-3-amine (0.88 g, 2.7 mmol) and TEA (0.6 mL, 4.0 mmol) in DCM (50 mL), tert-butoxycarbonyl anhydride (0.7 g, 3.2 mmol) was added and the mixture was heated at 40° C. under argon atmosphere for 20 h. DCM was added and washed with brine, dried over Na$_2$SO$_4$, filtered and concentrated. Purification by flash chromatography, silica gel, gradient hexane to 20% ethyl acetate, afforded the title compound (0.67 g, 65% yield).

Examples of Preparation of Intermediates of Formula (IX) and (XVI)

(rac)-(3,4-trans)-1-Benzyl-4-((3-phenyl prop-2-yn-1-yl)amino) pyrrolidin-3-ol

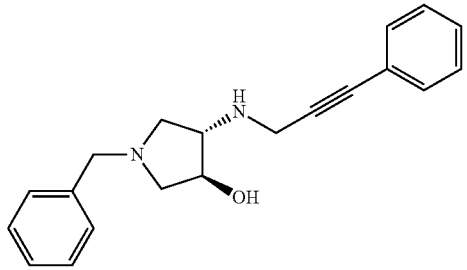 [SMILES: O[C@H]1CN(Cc2ccccc2)C[C@@H]1NCC#Cc1ccccc1]

A mixture of 3-benzyl-6-oxa-3-azabicyclo[3.1.0]hexane (374 mg, 2.1 mmol), LiClO$_4$ (1.1 g, 10.1 mol) and 3-phenylprop-2-yn-1-amine (350 mg, 2.67 mmol) in ACN (12 mL) was heated at 90° C. for 16 h. The solvent was evaporated, the crude was suspended in water and extracted with ethyl acetate. The combined organic extracts were dried over Na$_2$SO$_4$, filtered and concentrated. Purification by flash chromatography, silica gel, gradient hexane to 100% ethyl acetate, afforded the title compound (488 mg, 74% yield).

$^1$H-NMR (400 MHz, CDCl$_3$) δ ppm: 7.41 (m, 2H), 7.32 (m, 8H), 4.08 (m, 1H), 3.67 (AB system, 2H), 3.64 (AB system, 2H), 3.38 (m, 1H), 3.17 (dd, J$_1$=6.8 Hz, J$_2$=9.4 Hz, 1H), 2.74 (m, 2H), 2.21 (dd, J$_1$=5.6 Hz, J$_2$=9.5 Hz, 1H).

(3S,4S)-1-Benzyl-4-((4-phenylbut-3-yn-1-yl)amino) pyrrolidin-3-ol

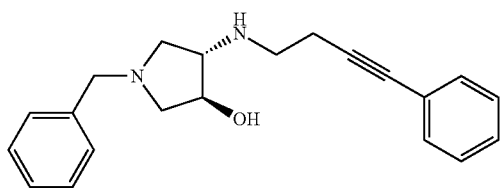 [SMILES: O[C@H]1CN(Cc2ccccc2)C[C@@H]1NCCC#Cc1ccccc1]

To a solution of 4-phenylbut-3-yn-1-yl-4-methylbenzenesulfonate (1.25 g, 4.0 mmol) and (3S,4S)-4-amino-1-benzylpyrrolidin-3-ol (760 mg, 3.95 mmol) in AcN (18 mL), $K_2CO_3$ (1.6 g, 11.9 mmol) was added and the solution was heated at 90° C. in a sealed tube for 20 h. The reaction was cooled at r.t., ethyl acetate was added and the mixture washed with water (10 mL), dried over $Na_2SO_4$, filtered and concentrated. Purification by flash chromatography, silica gel, DCM to 10% MeOH, afforded the title compound (650 mg, 51% yield).

$^1$H-NMR (400 MHz, $CDCl_3$) δ ppm: 7.40 (m, 2H), 7.31 (m, 8H), 4.07 (m, 1H), 3.67 (AB system, 2H), 3.23 (m, 1H), 3.18 (m, 1H), 2.89 (m, 2H), 2.77 (m, 2H), 2.64 (t, J=6.6 Hz, 2H), 2.24 (dd, $J_1$=5.0 Hz, $J_2$=9.2 Hz, 1H).

(rac)-(3,4-trans)-1-Benzyl-4-((3-(2-fluorophenyl) prop-2-yn-1-yl)amino) pyrrolidin-3-ol

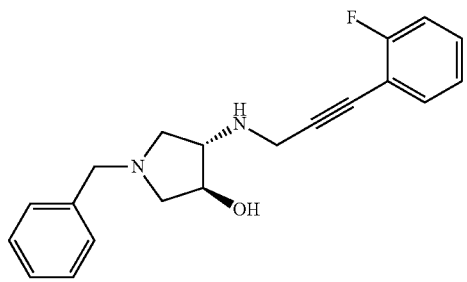 [SMILES: O[C@H]1CN(Cc2ccccc2)C[C@@H]1NCC#Cc1ccccc1F]

To a solution of (rac)-(3,4-trans)-4-amino-1-benzylpyrrolidin-3-ol (1.5 g, 7.8 mmol) in MeOH (70 mL) under nitrogen atmosphere, 3-(2-fluorophenyl)propiolaldehyde (1.27 g, 8.58 mmol) was added and the reaction mixture was stirred at r.t. for two hours. $NaBH_4$ (0.47 g, 12.47 mmol) was slowly added (caution, exothermic reaction!) and the mixture was stirred at r.t. for 1 h. The solvent was removed under vacuum and the crude residue was dissolved in DCM and succesively washed with $NaHCO_3$ aqueous saturated solution and brine. The organic phase was dried over $Na_2SO_4$, filtered and evaporated. Purification by flash chromatography, silica gel, DCM to 10% MeOH, afforded the title compound (1.81 g, 71% yield).

$^1$H-NMR (400 MHz, $CDCl_3$) δ ppm: 7.40 (m, 1H), 7.31 (m, 6H), 7.07 (m, 2H), 4.09 (m, 1H), 3.72 (AB system, 2H), 3.65 (AB system, 2H), 3.41 (m, 1H), 3.18 (dd, $J_1$=6.9 Hz, $J_2$=9.5 Hz, 1H), 2.75 (m, 2H), 2.24 (dd, $J_1$=5.5 Hz, $J_2$=9.5 Hz, 1H).

(rac)-tert-Butyl((3,4-trans)-1-benzyl-4-hydroxypyrrolidin-3-yl)(3-phenyl-prop-2-yn-1-yl)carbamate

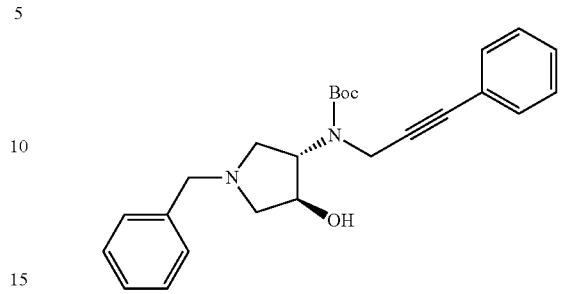

To a solution of (rac)-(3,4-trans)-1-benzyl-4-((3-phenyl-prop-2-yn-1-yl)amino)pyrrolidin-3-ol (1.69 g, 5.5 mmol) and TEA (1.2 mL, 8.6 mmol) in DCM (90 mL), a solution of tert-butoxycarbonyl anhydride (1.3 g, 6.1 mmol) in DCM (10 mL) was added and the mixture was stirred at r.t. under argon atmosphere for 20 h. DCM was added and the organic phase was washed with brine, dried over $Na_2SO_4$, filtered and concentrated. Purification by flash chromatography, silica gel, gradient hexane to 100% ethyl acetate, afforded the title compound (1.83 g, 82% yield).

$^1$H-NMR (500 MHz, $CDCl_3$) δ ppm: 7.32 (m, 10H), 4.31 (m, 4H), 3.66 (AB system, 2H), 2.95 (m, 3H), 2.55 (m, 1H), 1.52 (s, 9H).

(rac)-(3a,6a-cis)-5-Benzyl-3-(3-phenyl prop-2-yn-1-yl)hexahydro-2H-pyrrolo[3,4-d]oxazol-2-one

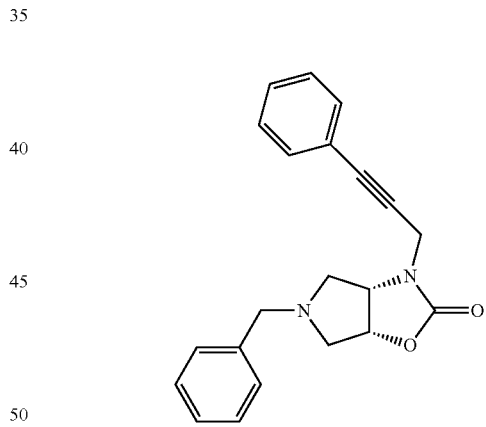

To a solution of (rac)-tert-butyl ((3,4-trans)-1-benzyl-4-hydroxypyrrolidin-3-yl)(3-phenyl-prop-2-yn-1-yl)carbamate (1.83 g, 4.5 mmol) in dry DCM (100 mL) cooled at 0° C., TEA (1.3 mL, 9.0 mmol) was added and stirred for 10 min; then, methanesulfonyl chloride (0.43 mL, 5.4 mmol) was added dropwise at 0° C. and the reaction mixture was allowed to warm to r.t. and stirred for 65 h. DCM was added and the organic phase was washed with saturated solution of $NaHCO_3$ and brine, dried over $Na_2SO_4$ and filtered. The solvent was evaporated to afford the title compound (1.85 g, 96% yield) that was used in the next step without further purification.

$^1$H-NMR (400 MHz, $CDCl_3$) δ ppm: 7.33 (m, 10H), 4.97 (dd, $J_1$=4.8 Hz, $J_2$=7.9 Hz, 1H), 4.60 (d AB system, 1H), 4.43 (dd, $J_1$=4.8 Hz, $J_2$=7.9 Hz, 1H), 4.05 (d AB system, 1H), 3.68 (AB system, 2H), 3.22 (t, J=11.2 Hz, 2H), 2.37 (dd, J₁=4.8 Hz, J₂=11.2 Hz, 1H), 2.22 (dd, J₁=4.8 Hz, J₂=10.8 Hz, 1H).

(rac)-(3,4-cis)-1-Benzyl-4-((3-phenylprop-2-yn-1-yl)amino)pyrrolidin-3-ol

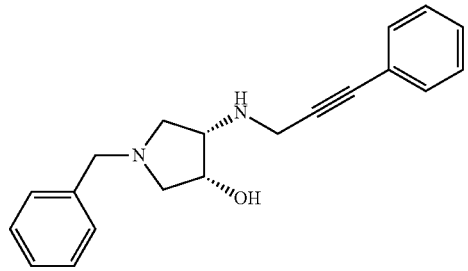 [SMILES: O[C@@H]1CN(Cc2ccccc2)C[C@@H]1NCC#Cc1ccccc1]

To a solution of (rac)-(3a,6a-cis)-5-benzyl-3-(3-phenylprop-2-yn-1-yl)hexahydro-2H-pyrrolo[3,4-d]oxazol-2-one (1.85 g, 5.67 mmol) in MeOH (50 mL), a solution of NaOH (6.6 g, 167 mmol) in a mixture of MeOH:water (1:1, 10 mL) was added and the mixture was refluxed for 2 h. MeOH was evaporated, water was added and the mixture was extracted with ethyl acetate. The organic phase was washed with brine, dried over $Na_2SO_4$, filtered and concentrated to afford the title compound (1.3 g, 76% yield), which was used in the next step without further purification.

$^1$H-NMR (500 MHz, $CDCl_3$) δ ppm: 7.32 (m, 10H), 4.22 (m, 1H), 3.68 (AB system, 2H), 3.65 (m, 2H), 3.45 (m, 1H), 2.92 (dd, J₁=5.7 Hz, J₂=10.4 Hz, 1H), 2.87 (dd, J₁=7.1 Hz, J₂=9.2 Hz, 1H), 2.64 (dd, J₁=2.8 Hz, J₂=10.4 Hz, 1H), 2.53 (dd, J₁=6.3 Hz, J₂=9.2 Hz, 1H).

Examples of Preparation of Compounds of General Formula (I)

HPLC analysis conditions: column Agilent Eclipse XDB-C18, 4.6×150 mm, 5 m; flux 1 mL/min; mobile phase A ($H_2O$+0.05% TFA), B (ACN); 1/gradient 5% to 95% B in 7 min, 2/isocratic 95% B 5 min.

Hydrochloride preparation: in those cases where the compounds were isolated as the hydrochloride salt, the corresponding amine was dissolved in ethyl acetate or a mixture or ethyl acetate and MeOH, and a 1.25 M solution of HCl in ethanol (1 equiv.) was added. After 30 min of stirring, the mixture was concentrated under reduced pressure to afford the hydrochloride.

Example 1: (rac)-(5a,8a-trans)-7-benzyl-3-phenyl-5,5a,6,7,8,8a-hexahydro-4H-pyrrolo[3,4-e][1,2,3]triazolo[1,5-a]pyrazine

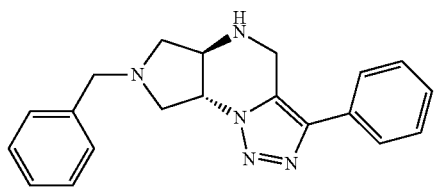 [SMILES: c1ccc(CN2C[C@@H]3[C@@H](C2)NCc2c(-c4ccccc4)nnn23)cc1]

A solution of (rac)-(3,4-trans)-4-azido-1-benzyl-N-(3-phenylprop-2-yn-1-yl)pyrrolidin-3-amine (450 mg, 1.36 mmol) in xylene (45 mL) was heated at 135° C. for 20 h. The reaction mixture was cooled at r.t. and the solvent evaporated. Purification by flash chromatography, silica gel, gradient from DCM to 5% MeOH afforded the title compound (240 mg, 53% yield). HPLC retention time: 4.97 min; HRMS: 332.1887 (M+H).

Example 2: (rac)-(5a,8a-cis)-7-benzyl-3-phenyl-5,5a,6,7,8,8a-hexahydro-4H-pyrrolo[3,4-e][1,2,3]triazolo[1,5-a]pyrazin-4-one

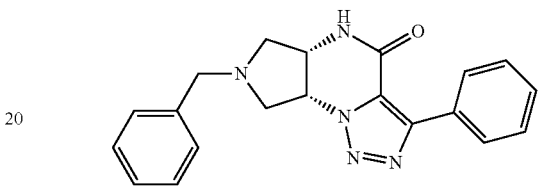

A solution of (rac)-N-((3,4-cis)-4-azido-1-benzylpyrrolidin-3-yl)-3-phenylpropiolamide (2.2 g, 6.3 mmol) in xylene (230 mL) was heated at 115° C. for 20 h. The reaction mixture was cooled at r.t. and the solvent evaporated. Purification by flash chromatography, silica gel, gradient hexane to 100% ethyl acetate, afforded the title compound (2.06 g, 93% yield). HPLC retention time: 5.33 min; HRMS: 346.1662 (M+H).

An method analogous to this was used for the preparation of examples 21-22, 28-30 and 34-35.

Example 3: (rac)-(5a,8a-cis)-7-benzyl-3-phenyl-5,5a,6,7,8,8a-hexahydro-4H-pyrrolo [3,4-e][1,2,3]triazolo[1,5-a]pyrazine

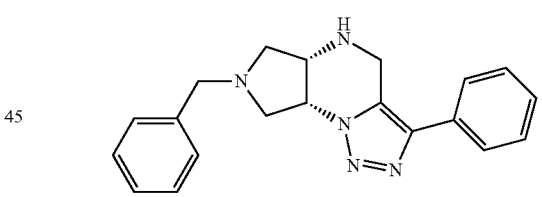

To dry THF (1 mL) under argon atmosphere, $LiAlH_4$ 1M solution in THF (3.5 mL, 3.5 mmol) was added at 0° C. followed by the addition of a solution of (rac)-(5a,8a-cis)-7-benzyl-3-phenyl-5,5a,6,7,8,8a-hexahydro-4H-pyrrolo[3,4-e][1,2,3]triazolo[1,5-a]pyrazin-4-one (0.40 g, 1.16 mmol) in dry THF (25 mL). The reaction mixture was heated at reflux for 15 h. The reaction was quenched by the sequential treatment at 0° C. with $H_2O$ (2 mL) and 5% NaOH solution (1 mL). The reaction mixture was filtered through a pad of Celite and the filtrate was concentrated and extracted with DCM/water. The organic phase was dried over $MgSO_4$ and concentrated. Purification by flash chromatography, silica gel, gradient hexane to 100% ethyl acetate, afforded the title compound (230 mg, 60% yield) as white solid. HPLC retention time: 5.13 min; HRMS: 332.1862 (M+H).

This method was also used for the preparation of examples of formula (I): 12-15. In the case of example 15 an additional chiral HPLC semipreparative purification of example 1 was done. Conditions: column Chiralcel OD-H, hexane:ethanol (70:30), flux: 3.3 mL/min, injection volume: 400 μl (conc. 10 mg/mL in ethanol). Retention time: 12.2 min (the other enantiomer: 10.4 min).

Example 4: (rac)-1-((5a,8a-trans)-7-benzyl-3-phenyl-6,7,8,8a-tetrahydro-4H-pyrrolo[3,4-e][1,2,3]triazolo[1,5-a]pyrazin-5(5aH)-yl)ethanone

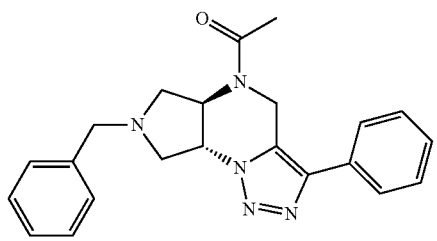 [SMILES: CC(=O)N1Cc2c(-c3ccccc3)nnn2[C@@H]2CN(Cc3ccccc3)C[C@H]21]

To a solution of (rac)-(5a,8a-trans)-7-benzyl-3-phenyl-5,5a,6,7,8,8a-hexahydro-4H-pyrrolo[3,4-e][1,2,3]triazolo[1,5-a]pyrazine (obtained in example 3, 50 mg, 0.15 mmol) in dry DCM (5 mL) under argon atmosphere, DIPEA (39 mg, 0.30 mmol) and acetyl chloride (18 mg, 0.22 mmol) were added and the reaction mixture was stirred at r.t. for 20 h. DCM was added and washed with water and brine. The organic layer was dried over $Na_2SO_4$, filtered and concentrated. Purification by flash chromatography, silica gel, gradient from hexane to 100% ethyl acetate, afforded the title compound (40 mg, 71% yield). HPLC retention time: 5.21 min; HRMS: 370.1982 (M+H).

Example 5: (rac)-(5a,8a-cis)-7-benzyl-3-phenyl-5-propyl-5,5a,6,7,8,8a-hexahydro-4H-pyrrolo[3,4-e][1,2,3]triazolo[1,5-a]pyrazin-4-one

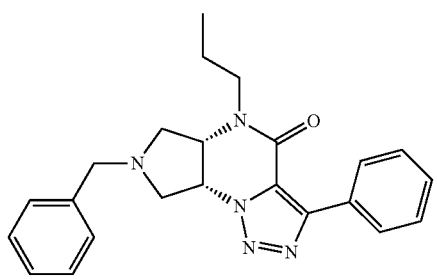 [SMILES: CCCN1C(=O)c2c(-c3ccccc3)nnn2[C@@H]2CN(Cc3ccccc3)C[C@@H]21]

To a suspension of NaH (10 mg, 0.27 mmol, 60% in mineral oil) in dry THF (1 mL) cooled at 0° C. under argon, a solution of (rac)-(5a,8a-cis)-7-benzyl-3-phenyl-5,5a,6,7,8,8a-hexahydro-4H-pyrrolo[3,4-e][1,2,3]triazolo[1,5-a]pyrazin-4-one (obtained in example 2, 55 mg, 0.16 mmol) in dry THF (3 mL) was added. The resulting mixture was stirred at r.t. for 30 min, 1-iodopropane (41 mg, 0.24 mmol) was added and the suspension further stirred at r.t. for 20 h. Water was added and the mixture was extracted with DCM. The organic phase was dried over $Na_2SO_4$, filtered and concentrated. Purification by flash chromatography, silica gel, gradient hexane to 100% ethyl acetate, afforded the title compound (41 mg, 67% yield). HPLC retention time: 5.88 min; HRMS: 410.1979 (M+Na).

This method was used for the preparation of examples 17, 20, 33 and 37.

Example 6: (rac)-(5a,8a-trans)-tert-butyl-3-phenyl-6,7,8,8a-tetrahydro-4H-pyrrolo[3,4-e][1,2,3]triazolo[1,5-a]pyrazine-5(5aH)-carboxylate

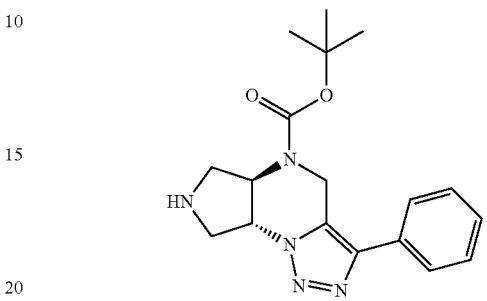

A mixture of (rac)-(5a,8a-trans)-tert-butyl-7-benzyl-3-phenyl-6,7,8,8a-tetrahydro-4H-pyrrolo[3,4-e][1,2,3]triazolo[1,5-a]-pyrazine-5(5aH)-carboxylate (360 mg, 0.83 mmol), ammonium formate (630 mg, 10.0 mmol), and Pd 10% on carbon (72 mg, 20% w/w) in MeOH (60 mL) was refluxed for 2 h under nitrogen atmosphere. The mixture was cooled to room temperature and filtered through a plug of Celite. The solvent was removed under vacuum and the residue was suspended in DCM, filtered and evaporated, to afford the title product (280 mg, 98% yield), that was used in the next step without further purification. $^1$H-NMR (400 MHz, $CDCl_3$) δ ppm: 8.15 (bs, 1H), 7.75 (m, 2H), 7.49 (m, 2H), 7.39 (m, 1H), 5.01 (AB System, 2H), 4.51 (m, 1H), 4.03 (dd, $J_1$=7.5 Hz, $J_2$=10.4 Hz, 1H), 3.90 (m, 1H), 3.61 (m, 1H), 3.52 (m, 2H), 1.53 (s, 9H).

Example 7: (rac)-(5a,8a-trans)-tert-butyl-7-(4-fluorobenzyl)-3-phenyl-6,7,8,8a-tetrahydro-4H-pyrrolo[3,4-e][1,2,3]triazolo[1,5-a]pyrazine-5(5aH)-carboxylate

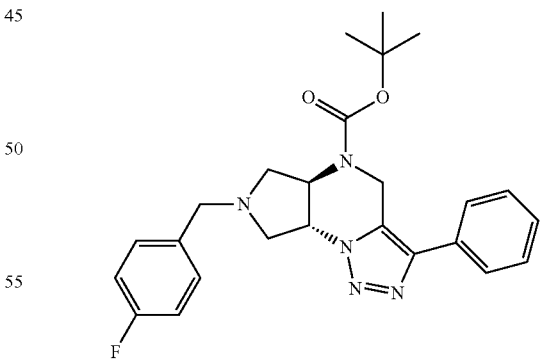

To a suspension of (rac)-(5a,8a-trans)-tert-butyl-3-phenyl-6,7,8,8a-tetrahydro-4H-pyrrolo[3,4-e][1,2,3]-triazolo[1,5-a]-pyrazine-5(5aH)-carboxylate (obtained in example 6, 70 mg, 0.20 mmol) in DCE (4 mL), 4-fluorobenzaldehyde (31 mg, 0.24 mmol) and $NaBH(OAc)_3$ (65 mg, 0.31 mmol) were added and the reaction mixture was stirred at r.t. for 20 h. DCM was added and the mixture was washed with water and brine. The organic phase was dried over $Na_2SO_4$, filtered and concentrated. Purification by flash chromatography, silica gel, gradient hexane to 100% ethyl acetate, afforded the title compound (50 mg, 54% yield). $^1$H-NMR (400 MHz, CDCl$_3$) δ ppm: 7.74 (m, 2H), 7.48 (m, 2H), 7.38 (m, 1H), 7.33 (m, 2H), 7.05 (m, 2H), 4.97 (AB system, 2H), 4.48 (m, 1H), 3.91 (AB system, 2H), 3.67 (m, 2H), 3.58 (m, 1H), 3.41 (t, J=9.7 Hz, 1H), 3.29 (t, J=9.7 Hz, 1H), 1.48 (s, 9H).

Example 8: (rac)-(5a,8a-trans)-7-(4-fluorobenzyl)-3-phenyl-5,5a,6,7,8,8a-hexahydro-4H-pyrrolo[3,4-e][1,2,3]triazolo[1,5-a]pyrazine, hydrochloride

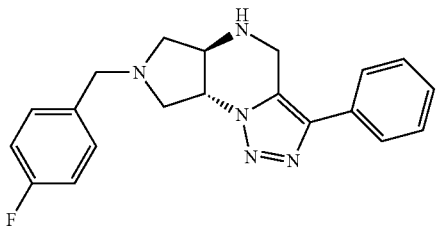 [SMILES: Fc1ccc(CN2C[C@@H]3[C@@H](C2)NCc2c(-c4ccccc4)nnn23)cc1]

To a suspension of (rac)-(5a,8a-trans)-tert-butyl-7-(4-fluorobenzyl)-3-phenyl-6,7,8,8a-tetrahydro-4H-pyrrolo[3,4-e][1,2,3]-triazolo[1,5-a]-pyrazine-5(5aH)-carboxylate (obtained in example 7, 47 mg, 0.10 mmol) in dioxane (0.25 mL), a 4M HCl solution in dioxane (0.34 mL, 1.35 mmol) was added and the mixture was stirred at r.t. for 65 h. The solvent was removed under vacuum to afford the title compound (42 mg, 98% yield). HPLC retention time: 5.11 min; HRMS: 350.1795 (M+H).

Example 9: (rac)-(5a,8a-trans)-7-benzyl-3-phenyl-5-propyl-5,5a,6,7,8,8a-hexahydro-4H-pyrrolo[3,4-e][1,2,3]triazolo[1,5-a]pyrazine

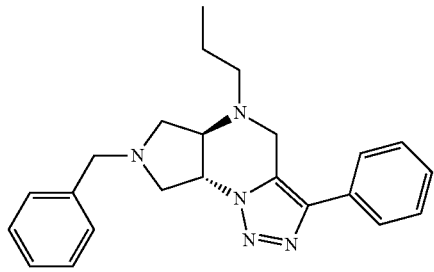 [SMILES: CCCN1Cc2c(-c3ccccc3)nnn2[C@@H]2CN(Cc3ccccc3)C[C@H]21]

To a solution of (rac)-(5a,8a-trans)-7-benzyl-3-phenyl-5,5a,6,7,8,8a-hexahydro-4H-pyrrolo[3,4-e][1,2,3]triazolo[1,5-a]pyrazine (50 mg, 0.15 mmol) in DCE (3 mL), acetic acid (9 mg, 0.15 mmol), propionaldehyde (11 mg, 0.18 mmol) and NaBH(OAc)$_3$ (48 mg, 0.23 mmol) were added and the reaction mixture was stirred at r.t. for 4 h. NaHCO$_3$ aqueous saturated solution was added and the mixture was extracted with DCM. The organic phase was washed with brine, dried over Na$_2$SO$_4$ and filtered. The solvent was evaporated and the crude residue purified by flash chromatography, silica gel, gradient hexane to 40% ethyl acetate, to afford the title compound (39 mg, 69% yield). HPLC retention time: 5.98 min; HRMS: 374.2350 (M+H).

Example 10: (rac)-(5a,8a-trans)-3-phenyl-5-propyl-5,5a,6,7,8,8a-hexahydro-4H-pyrrolo[3,4-e][1,2,3]triazolo[1,5-a]pyrazine, hydrochloride

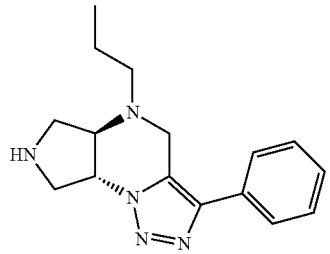 [SMILES: CCCN1Cc2c(-c3ccccc3)nnn2[C@@H]2CNC[C@H]21]

To a solution of (rac)-(5a,8a-trans)-7-benzyl-3-phenyl-5-propyl-5,5a,6,7,8,8a-hexahydro-4H-pyrrolo[3,4-e][1,2,3]triazolo[1,5-a]pyrazine (obtained in example 9, 120 mg, 0.32 mmol) in MeOH (15 mL), a 1.25 M HCl solution in MeOH (257 μl, 0.32 mmol) was added under argon atmosphere. The resulting solution was added to a suspension of Pd 10% on carbon (25 mg, 20% w/w) in MeOH (1 mL) under hydrogen atmosphere. The resulting mixture was stirred under hydrogen atmosphere for 20 h. The reaction mixture was purged with argon and filtered through a plug of Celite and washed with MeOH. The solvent was removed under vacuum to afford the title compound (93 mg, 91% yield). HPLC retention time: 5.11 min; HRMS: 284.1875 (M+H).

This method was used for the preparation of example 36.

Example 11: (rac)-(5a,8a-trans)-7-pentyl-3-phenyl-5-propyl-5,5a,6,7,8,8a-hexahydro-4H-pyrrolo[3,4-e][1,2,3]triazolo[1,5-a]pyrazine

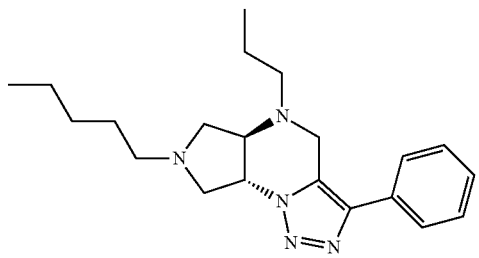 [SMILES: CCCCCN1C[C@@H]2[C@@H](C1)n1nnc(-c3ccccc3)c1CN2CCC]

To a suspension of (rac)-(5a,8a-trans)-3-phenyl-5-propyl-5,5a,6,7,8,8a-hexahydro-4H-pyrrolo[3,4-e][1,2,3]triazolo[1,5-a]pyrazine hydrochloride (obtained in example 10, 45 mg, 0.14 mmol) in DCE (3 mL), DIPEA (19 mg, 0.14 mmol) was added and the mixture was stirred for 15 min. To the resulting solution, acetic acid (8.5 mg, 0.14 mmol), pentanal (15 mg, 0.17 mmol) and NaBH(OAc)$_3$ (48 mg, 0.23 mmol) were added and the reaction mixture was stirred at r.t. for 2 h. NaHCO$_3$ aqueous saturated solution was added and the mixture was extracted with DCM. The organic phase was washed with water and brine, dried over Na$_2$SO$_4$ and filtered. The solvent was evaporated to afford a crude residue that was purified by flash chromatography, silica gel, gradient hexane to 100% ethyl acetate, to give the title compound (42 mg, 84% yield). HPLC retention time: 6.07 min; HRMS: 354.2669 (M+H).

This method was used for the preparation of examples 16, 18-19, 23-27 and 31-32.

Table I below, discloses compounds prepared according to the aforementioned methods:

TABLE I

| EX | Structure | Name | HPLC (retention time, min) | HRMS |
|---|---|---|---|---|
| 1 | 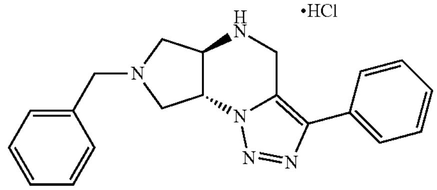 [SMILES: Cl ; c1ccc(CN2C[C@@H]3[C@@H](C2)NCc2c(-c4ccccc4)nnn23)cc1] | (rac) (5a,8a-trans)-7-benzyl-3-phenyl-5,5a,6,7,8,8a-hexahydro-4H-pyrrolo[3,4-e][1,2,3]triazolo[1,5-a]pyrazine, hydrochloride | 4.97 | 332.1887 (M + H) |
| 2 | 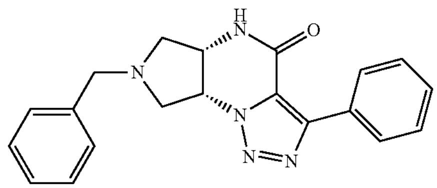 [SMILES: O=C1N[C@H]2CN(Cc3ccccc3)C[C@H]2n2nnc(-c3ccccc3)c21] | (rac)-(5a,8a-cis)-7-benzyl-3-phenyl-5,5a,6,7,8,8a-hexahydro-4H-pyrrolo[3,4-e][1.2.3]triazolo[1,5-a]pyrazin-4-one | 5.33 | 346.1662 (M + H) |
| 3 | 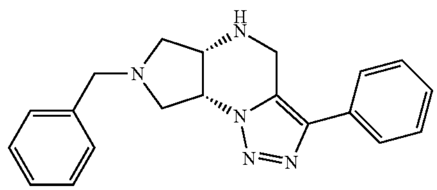 [SMILES: c1ccc(CN2C[C@@H]3NCc4c(-c5ccccc5)nnn4[C@@H]3C2)cc1] | (rac) (5a,8a-cis)-7-benzyl-3-phenyl-5,5a,6,7,8,8a-hexahydro-4H-pyrrolo[3,4-e][1,2,3]triazolo[1,5-a]pyrazine | 5.13 | 332.1862 (M + H) |
| 4 | 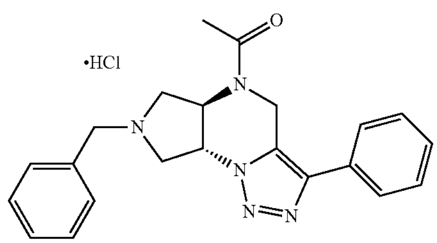 | (rac) 1-((5a,8a-trans)-7-benzyl-3-phenyl-6,7,8,8a-tetrahydro-4H-pyrrolo[3,4-e][1,2,3]triazolo[1,5-a]pyrazin-5(5aH)-yl)ethanone, hydrochloride | 5.21 | 370.1982 (M + H) |
| 5 | 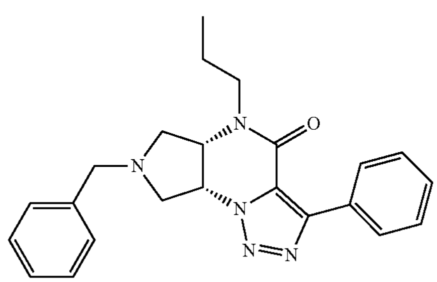 [SMILES: CCCN1C(=O)c2c(-c3ccccc3)nnn2[C@@H]2CN(Cc3ccccc3)C[C@@H]21] | (rac)-(5a,8a-cis)-7-benzyl-3-phenyl-5-propyl-5,5a,6,7,8,8a-hexahydro-4H-pyrrolo[3,4-e][1.2.3]triazolo[1,5-a]pyrazin-4-one | 5.88 | 410.1979 (M + Na) |
| 6 | 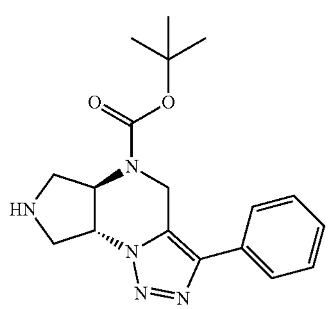 [SMILES: CC(C)(C)OC(=O)N1Cc2c(-c3ccccc3)nnn2[C@@H]2CNC[C@H]21] | (rac)-(5a,8a-trans)-tert-butyl-3-phenyl-6,7,8,8a-tetrahydro-4H-pyrrolo[3,4-e][1,2,3]triazolo[1,5-a]pyrazine-5(5aH)-carboxylate | | |

TABLE I-continued

| EX | Structure | Name | HPLC (retention time, min) | HRMS |
|---|---|---|---|---|
| 7 | 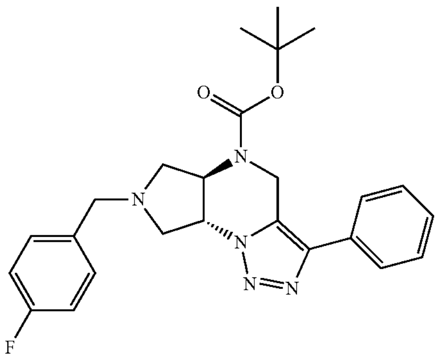 [SMILES: CC(C)(C)OC(=O)N1Cc2c(-c3ccccc3)nnn2[C@@H]2CN(Cc3ccc(F)cc3)C[C@H]21] | (rac)-(5a,8a-trans)-tert-butyl-7-(4-fluorobenzyl)-3-phenyl-6,7,8,8a-tetrahydro-4H-pyrrolo[3,4-e][1,2,3]triazolo[1,5-a]pyrazine-5(5aH)-carboxylate | | |
| 8 | •HCl | (rac) (5a,8a-trans)-7-(4-fluorobenzyl)-3-phenyl-5,5a,6,7,8,8a-hexahydro-4H-pyrrolo[3,4-e][1,2,3]triazolo[1,5-a]pyrazine, hydrochloride | 5.11 | 350.1795 (M + H) |
| 9 | •HCl | (rac) (5a,8a-trans)-7-benzyl-3-phenyl-5-propyl-5,5a,6,7,8,8a-hexahydro-4H-pyrrolo[3,4-e][1,2,3]triazolo[1,5-a]pyrazine, hydrochloride | 5.98 | 374.2350 (M + H) |
| 10 | •HCl | (rac) (5a,8a-trans)-3-phenyl-5-propyl-5,5a,6,7,8,8a-hexahydro-4H-pyrrolo[3,4-e][1,2,3]triazolo[1,5-a]pyrazine, hydrochloride | 5.11 | 284.1875 (M + H) |
| 11 | •HCl | (rac) (5a,8a-trans)-7-pentyl-3-phenyl-5-propyl-5,5a,6,7,8,8a-hexahydro-4H-pyrrolo[3,4-e][1,2,3]triazolo[1,5-a]pyrazine, hydrochloride | 6.07 | 354.2669 (M + H) |

TABLE I-continued

| EX | Structure | Name | HPLC (retention time, min) | HRMS |
|---|---|---|---|---|
| 12 | 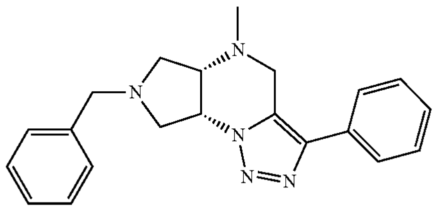 [SMILES: CN1Cc2c(-c3ccccc3)nnn2[C@@H]2CN(Cc3ccccc3)C[C@@H]21] | (rac) (5a,8a-cis)-7-benzyl-5-methyl-3-phenyl-5,5a,6,7,8,8a-hexahydro-4H-pyrrolo[3,4-e][1,2,3]triazolo[1,5-a]pyrazine | 5.37 | 346.2036 (M + H) |
| 13 | 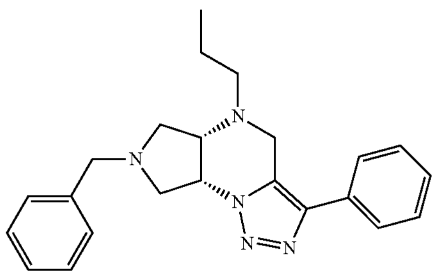 [SMILES: CCCN1Cc2c(-c3ccccc3)nnn2[C@@H]2CN(Cc3ccccc3)C[C@@H]21] | (rac) (5a,8a-cis)-7-benzyl-3-phenyl-5-propyl-5,5a,6,7,8,8a-hexahydro-4H-pyrrolo[3,4-e][1,2,3]triazolo[1,5-a]pyrazine | 6.03 | 374.2368 (M + H) |
| 14 | 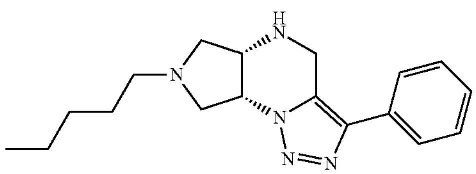 [SMILES: CCCCCN1C[C@@H]2NCc3c(-c4ccccc4)nnn3[C@@H]2C1] | (rac) (5a,8a-cis)-7-pentyl-3-phenyl-5,5a,6,7,8,8a-hexahydro-4H-pyrrolo[3,4-e][1,2,3]triazolo[1,5-a]pyrazine | 5.33 | 312.2179 (M + H) |
| 15 | 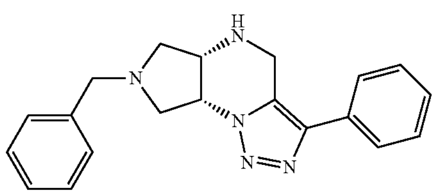 [SMILES: c1ccc(CN2C[C@@H]3NCc4c(-c5ccccc5)nnn4[C@@H]3C2)cc1] | (5aS,8aR)-7-benzyl-3-phenyl-5,5a,6,7,8,8a-hexahydro-4H-pyrrolo[3,4-e][1,2,3]triazolo[1,5-a]pyrazine | 5.12 | 332.1891 (M + H) |
| 16 | 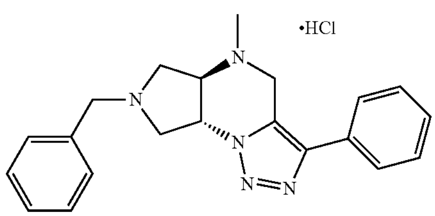 [SMILES: CN1Cc2c(-c3ccccc3)nnn2[C@@H]2CN(Cc3ccccc3)C[C@H]21 ; Cl] | (rac) (5a,8a-trans)-7-benzyl-5-methyl-3-phenyl-5,5a,6,7,8,8a-hexahydro-4H-pyrrolo[3,4-e][1,2,3]triazolo[1,5-a]pyrazine, hydrochloride | 5.34 | 346.2022 (M + H) |
| 17 | 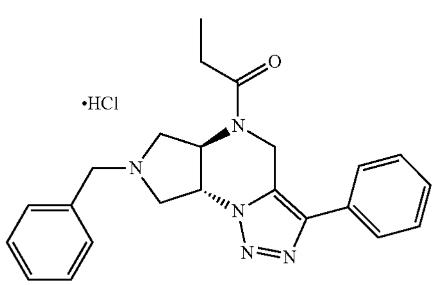 [SMILES: CCC(=O)N1Cc2c(-c3ccccc3)nnn2[C@@H]2CN(Cc3ccccc3)C[C@H]21 ; Cl] | (rac) 1-((5a,8a-trans)-7-benzyl-3-phenyl-6,7,8,8a-tetrahydro-4H-pyrrolo[3,4-e][1,2,3]triazolo[1,5-a]pyrazin-5(5aH)-yl)propan-1-one, hydrochloride | 5.47 | 388.2134 (M + H) |

TABLE I-continued

| EX | Structure | Name | HPLC (retention time, min) | HRMS |
|----|-----------|------|------|------|
| 18 | 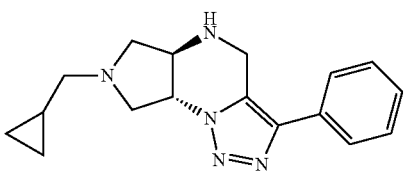 | (rac) (5a,8a-trans)-7-(cyclopropyl-methyl)-3-phenyl-5,5a,6,7,8,8a-hexahydro-4H-pyrrolo[3,4-e][1,2,3]triazolo[1,5-a]pyrazine, hydrochloride | 4.54 | 296.1888 (M + H) |
| 19 | 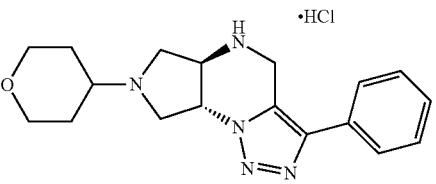 [SMILES: Cl ; c1ccc(-c2nnn3c2CN[C@@H]2CN(C4CCOCC4)C[C@H]23)cc1] | (rac) (5a,8a-trans)-3-phenyl-7-(tetrahydro-2H-pyran-4-yl)-5,5a,6,7,8,8a-hexahydro-4H-pyrrolo[3,4-e][1,2,3]triazolo[1,5-a]pyrazine, hydrochloride | 4.40 | 326.1996 (M + H) |
| 20 | 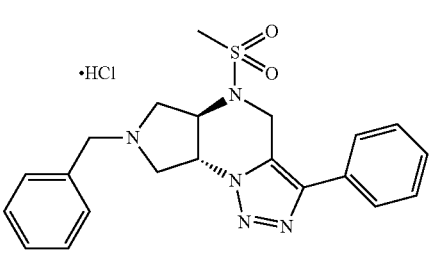 [SMILES: CS(=O)(=O)N1Cc2c(-c3ccccc3)nnn2[C@@H]2CN(Cc3ccccc3)C[C@H]21 ; Cl] | (rac) (5a,8a-trans)-7-benzyl-5-(methylsulfonyl)-3-phenyl-5,5a,6,7,8,8a-hexahydro-4H-pyrrolo[3,4-e][1,2,3]triazolo[1,5-a]pyrazine, hydrochloride | 5.64 | 410.1637 (M + H) |
| 21 | 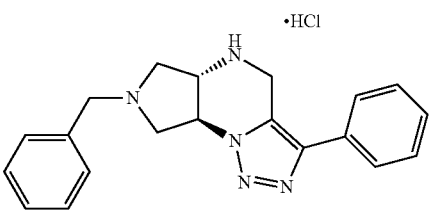 [SMILES: Cl ; c1ccc(CN2C[C@@H]3NCc4c(-c5ccccc5)nnn4[C@H]3C2)cc1] | (5aS,8aS)-7-benzyl-3-phenyl-5,5a,6,7,8,8a-hexahydro-4H-pyrrolo[3,4-e][1,2,3]triazolo[1,5-a]pyrazine, hydrochloride | 4.98 | 332.1875 (M + H) |
| 22 | 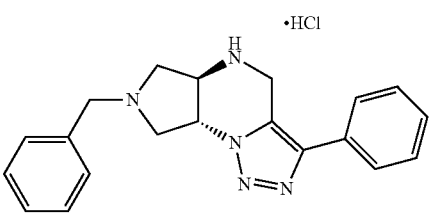 [SMILES: Cl ; c1ccc(CN2C[C@@H]3[C@@H](C2)NCc2c(-c4ccccc4)nnn23)cc1] | (5aR,8aR)-7-benzyl-3-phenyl-5,5a,6,7,8,8a-hexahydro-4H-pyrrolo[3,4-e][1,2,3]triazolo[1,5-a]pyrazine, hydrochloride | 4.99 | 332.1879 (M + H) |
| 23 | 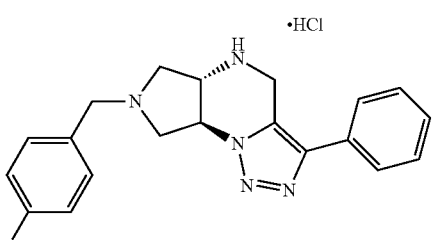 | (5aS,8aS)-7-(4-fluorobenzyl)-3-phenyl-5,5a,6,7,8,8a-hexahydro-4H-pyrrolo[3,4-e][1,2,3]triazolo[1,5-a]pyrazine, hydrochloride | 5.09 | 350.1792 (M + H) |

TABLE I-continued

| EX | Structure | Name | HPLC (retention time, min) | HRMS |
|----|-----------|------|------|------|
| 24 | ·HCl | (5aR,8aR)-7-(4-fluorobenzyl)-3-phenyl-5,5a,6,7,8,8a-hexahydro-4H-pyrrolo[3,4-e][1,2,3]triazolo[1,5-a]pyrazine, hydrochloride | 5.10 | 350.1791 (M + H) |
| 25 | ·HCl | (5aR,8aR)-7-(4-chlorobenzyl)-3-phenyl-5,5a,6,7,8,8a-hexahydro-4H-pyrrolo[3,4-e][1,2,3]triazolo[1,5-a]pyrazine, hydrochloride | 5.38 | 366.1488 (M + H) |
| 26 | ·HCl | (5aR,8aR)-3-phenyl-7-(4-(trifluoromethyl)benzyl)-5,5a,6,7,8,8a-hexahydro-4H-pyrrolo[3,4-e][1,2,3]triazolo[1,5-a]pyrazine, hydrochloride | 5.64 | 400.1753 (M + H) |
| 27 | ·HCl | (5aR,8aR)-3-phenyl-7-((tetrahydro-2H-pyran-4-yl)methyl)-5,5a,6,7,8,8a-hexahydro-4H-pyrrolo[3,4-e][1,2,3]triazolo[1,5-a]pyrazine, hydrochloride | 4.52 | 340.2121 (M + H) |
| 28 | ·HCl | (rac) (5a,8a-trans)-7-benzyl-3-(2-fluorophenyl)-5,5a,6,7,8,8a-hexahydro-4H-pyrrolo[3,4-e][1,2,3]triazolo[1,5-a]pyrazine, hydrochloride | 4.99 | 350.1798 (M + H) |
| 29 | ·HCl | (5aR,8aR)-7-benzyl-3-(2-fluorophenyl)-5,5a,6,7,8,8a-hexahydro-4H-pyrrolo[3,4-e][1,2,3]triazolo[1,5-a]pyrazine, hydrochloride | 5.01 | 350.1797 (M + H) |

TABLE I-continued

| EX | Structure | Name | HPLC (retention time, min) | HRMS |
|---|---|---|---|---|
| 30 | 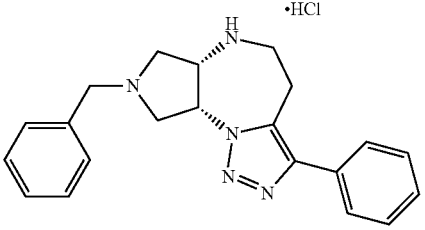 [SMILES: Cl ; c1ccc(CN2C[C@@H]3NCCc4c(-c5ccccc5)nnn4[C@@H]3C2)cc1] | (rac) (6a,9a-cis)-8-benzyl-3-phenyl-4,5,6,6a,7,8,9,9a-octahydropyrrolo[3,4-b][1,2,3]triazolo[1,5-d][1,4]diazepine, hydrochloride | 5.17 | 346.2032 (M + H) |
| 31 | 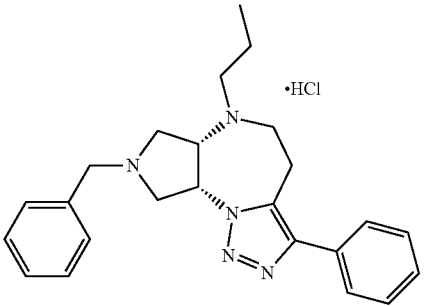 [SMILES: CCCN1CCc2c(-c3ccccc3)nnn2[C@@H]2CN(Cc3ccccc3)C[C@@H]21 ; Cl] | (rac) (6a,9a-cis)-8-benzyl-3-phenyl-6-propyl-4,5,6,6a,7,8,9,9a-octahydropyrrolo[3,4-b][1,2,3]triazolo[1,5-d][1,4]diazepine, hydrochloride | 6.17 | 410.2324 (M + Na) |
| 32 | 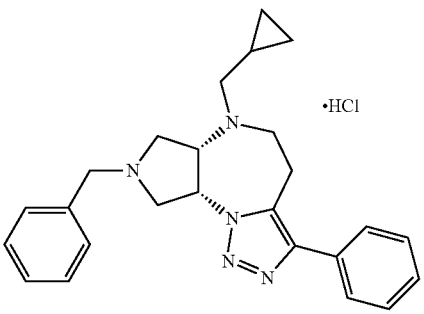 [SMILES: c1ccc(CN2C[C@@H]3[C@H](C2)N(CC2CC2)CCc2c(-c4ccccc4)nnn23)cc1 ; Cl] | (rac) (6a,9a-cis)-8-benzyl-6-(cyclopropylmethyl)-3-phenyl-4,5,6,6a,7,8,9,9a-octahydropyrrolo[3,4-b][1,2,3]triazolo[1,5-d][1,4]diazepine, hydrochloride | 6.17 | 400.2506 (M + H) |
| 33 | 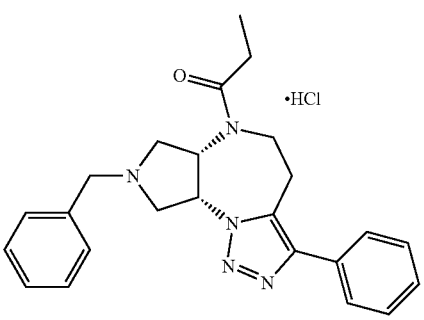 [SMILES: CCC(=O)N1CCc2c(-c3ccccc3)nnn2[C@@H]2CN(Cc3ccccc3)C[C@@H]21 ; Cl] | (rac) 1-((6a,9a-cis)-8-benzyl-3-phenyl-4,5,7,8,9,9a-hexahydropyrrolo[3,4-b][1,2,3]triazolo[1,5-d][1,4]diazepin-6(6aH)-yl)propan-1-one, hydrochloride | 5.68 | 424.2103 (M + H) |
| 34 | 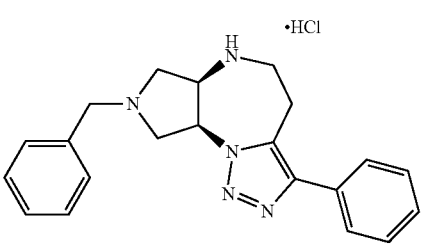 [SMILES: Cl ; c1ccc(CN2C[C@H]3NCCc4c(-c5ccccc5)nnn4[C@H]3C2)cc1] | (6aR,9aS)-8-benzyl-3-phenyl-4,5,6,6a,7,8,9,9a-octahydropyrrolo[3,4-b][1,2,3]triazolo[1,5-d][1,4]diazepine, hydrochloride | 5.14 | 346.2 (M + H) |

TABLE I-continued

| EX | Structure | Name | HPLC (retention time, min) | HRMS |
|---|---|---|---|---|
| 35 | 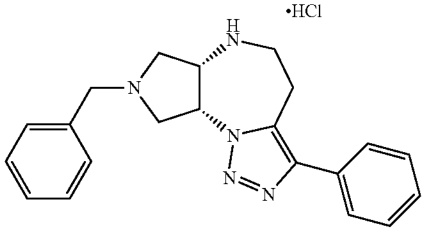 [SMILES: Cl ; c1ccc(CN2C[C@@H]3NCCc4c(-c5ccccc5)nnn4[C@@H]3C2)cc1] | (6aS,9aR)-8-benzyl-3-phenyl-4,5,6,6a,7,8,9,9a-octahydropyrrolo[3,4-b][1,2,3]triazolo[1,5-d][1,4]-diazepine, hydrochloride | 5.13 | 346.2 (M + H) |
| 36 | 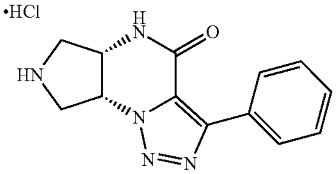 [SMILES: Cl ; O=C1N[C@H]2CNC[C@H]2n2nnc(-c3ccccc3)c21] | (rac)-(5a,8a-cis)-3-phenyl-5,5a,6,7,8,8a-hexahydro-4H-pyrrolo[3,4-e][1,2,3]triazolo[1,5-a]pyrazin-4-one, hydrochloride | 5.41 | 256.1205 (M + H) |
| 37 | 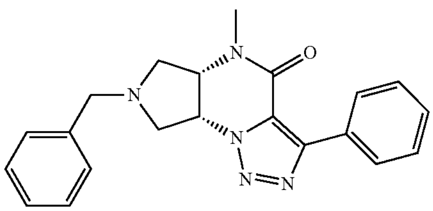 [SMILES: CN1C(=O)c2c(-c3ccccc3)nnn2[C@@H]2CN(Cc3ccccc3)C[C@@H]21] | (rac)-(5a,8a-cis)-7-benzyl-5-methyl-3-phenyl-5,5a,6,7,8,8a-hexahydro-4H-pyrrolo[3,4-e][1,2,3]triazolo[1,5-a]pyrazin-4-one | 5.36 | 382.1660 (M + Na) |

Biological Activity

Pharmacological Study

Brain membrane preparation and binding assays for the σ1-receptor were performed as described (DeHaven-Hudkins, D. L., L. C. Fleissner, and F. Y. Ford-Rice, 1992, Characterization of the binding of [$^3$H](+)pentazocine to a recognition sites in guinea pig brain, Eur. J. Pharmacol. 227, 371-378) with some modifications. Guinea pig brains were homogenized in 10 vols. (w/v) of Tris-HCl 50 mM 0.32 M sucrose, pH 7.4, with a Kinematica Polytron PT 3000 at 15000 r.p.m. for 30 s. The homogenate was centrifuged at 1000 g for 10 min at 4° C. and the supernatants collected and centrifuged again at 48000 g for 15 min at 4° C. The pellet was resuspended in 10 volumes of Tris-HCl buffer (50 mM, pH 7.4), incubated at 37° C. for 30 min, and centrifuged at 48000 g for 20 min at 4° C. Following this, the pellet was resuspended in fresh Tris-HCl buffer (50 mM, pH 7.4) and stored on ice until use.

The radioligand used was [$^3$H]-(+)-pentazocine at 5.0 nM and the final volume was 200 µl. The incubation was initiated with the addition of 100 µl of membrane at a final tissue concentration of approximately 5 mg tissue net weight/mL and the incubation time was 150 m. at 37° C. After incubation, the membranes were collected onto pretreated glass fiber filterplate (MultiScreen-FC, Millipore), with polyethylenimine 0.1%. The filters were washed two times with 200 µl of washing buffer (50 mM Tris Cl, pH=7.4) and then 25 µl of Ecoscint H liquid scintillation cocktail were added. Microplates were allowed to set for several hours and then quantified by liquid scintillation spectrophotometry (1450 Microbeta, Wallac). Nonspecific binding was determined with 1 µM haloperidol.

The results obtained for the examples are shown in table II.

TABLE II

| EX | $K_i$* (nM) |
|---|---|
| 1 | # |
| 2 | ### |
| 3 | ## |
| 4 | ## |
| 5 | ### |
| 6 | ### |
| 7 | ### |
| 8 | # |
| 9 | # |
| 10 | ### |
| 11 | # |
| 12 | # |
| 13 | ## |
| 14 | # |
| 15 | # |
| 16 | # |
| 17 | ## |
| 18 | ## |
| 19 | ### |
| 20 | ## |
| 21 | ### |
| 22 | # |
| 23 | ### |
| 24 | # |
| 25 | # |
| 26 | ## |
| 27 | ## |
| 28 | # |
| 29 | # |
| 30 | # |
| 31 | # |

TABLE II-continued

| EX | $K_i$* (nM) |
|---|---|
| 32 | # |
| 33 | ## |
| 34 | ## |
| 35 | # |
| 36 | ### |
| 37 | ### |

*$K_i$ values: # $K_i$ < 100; ## 100 < $K_i$ < 500; ### $K_i$ > 500

The invention claimed is:

1. A compound of formula (I):

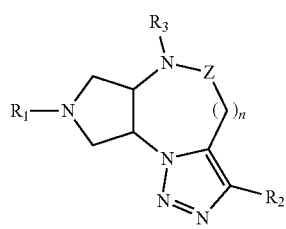

wherein $R_1$ is a H; a $C_{1-6}$ alkyl optionally substituted by at least one substituent selected from a halogen, $C_{1-3}$-alkoxy, $C_{1-3}$-alkyl, $C_{1-3}$-haloalkoxy, $C_{1-3}$-haloalkyl, trihaloalkyl or a hydroxyl group; a $C_{3-9}$ cycloalkyl optionally substituted by at least one substituent selected from a halogen, $C_{1-3}$-alkoxy, $C_{1-3}$-alkyl, $C_{1-3}$-haloalkoxy, $C_{1-3}$-haloalkyl, trihaloalkyl or a hydroxyl group; a 5 or 6-membered heterocycloalkyl having at least one heteroatom selected from O, N or S and being optionally substituted by at least one substituent selected from a halogen, $C_{1-3}$-alkoxy, $C_{1-3}$-haloalkoxy, $C_{1-3}$-haloalkyl, trihaloalkyl or a hydroxyl group; a 5 or 6-membered aryl optionally substituted by at least one substituent selected from a halogen, $C_{1-3}$-alkoxy, $C_{1-3}$ haloalkoxy, $C_{1-3}$-haloalkoxy, $C_{1-3}$-haloalkyl, trihaloalkyl or a hydroxyl group; a 5 or 6-membered heteroaryl having at least one heteroatom selected from O, N or S and being optionally substituted by at least one substituent selected from a halogen, $C_{1-3}$-alkoxy, $C_{1-3}$-haloalkoxy, $C_{1-3}$-haloalkyl, trihaloalkyl or a hydroxyl group; a —(C(R$_4$)$_2$)$_m$—C$_{3-9}$ cycloalkyl, the cycloalkyl group being optionally substituted by at least one substituent selected from a halogen, $C_{1-3}$-alkoxy, $C_{1-3}$-alkyl, $C_{1-3}$-haloalkoxy, $C_{1-3}$-haloalkyl, trihaloalkyl or a hydroxyl group; a —(C(R$_4$)$_2$)$_m$-heterocycloalkyl, the heterocycloalkyl group being a 5 or 6-membered ring having at least one heteroatom selected from O, N or S and being optionally substituted by at least one substituent selected from a halogen, $C_{1-3}$-alkoxy, $C_{1-3}$-alkyl, $C_{1-3}$-haloalkoxy, $C_{1-3}$-haloalkyl, trihaloalkyl or a hydroxyl group; a —(C(R$_4$)$_2$)$_m$-aryl, the aryl group being a 5 or 6-membered ring optionally substituted by at least one substituent selected from a halogen, $C_{1-3}$-alkoxy, $C_{1-3}$-alkyl, $C_{1-3}$-haloalkoxy, $C_{1-3}$-haloalkyl, trihaloalkyl or a hydroxyl group; or a —(C(R$_4$)$_2$)$_m$-heteroaryl, the heteroaryl group being a 5 or 6-membered ring having at least one heteroatom selected from O, N or S and being optionally substituted by at least one substituent selected from a halogen, $C_{1-3}$-alkoxy, $C_{1-3}$-alkyl, $C_{1-3}$-haloalkoxy, $C_{1-3}$-haloalkyl, trihaloalkyl or a hydroxyl group;

$R_2$ is a 5 or 6-membered aryl optionally substituted by at least one substituent selected from a halogen, $C_{1-3}$-alkoxy, $C_{1-3}$-alkyl, $C_{1-3}$-haloalkoxy, $C_{1-3}$-haloalkyl, trihaloalkyl or a hydroxyl group; or a substituted 5 or 6-membered heteroaryl optionally substituted by at least one substituent selected from a halogen, $C_{1-3}$-alkoxy, $C_{1-3}$-alkyl, $C_{1-3}$-haloalkoxy, $C_{1-3}$-haloalkyl, trihaloalkyl or a hydroxyl group;

$R_3$ is a H; a $C_{1-6}$ alkyl optionally substituted by at least one substituent selected from a halogen, $C_{1-3}$-alkoxy, $C_{1-3}$-alkyl, $C_{1-3}$-haloalkoxy, $C_{1-3}$-haloalkyl, trihaloalkyl or a hydroxyl group; —(C(R$_4$)$_2$)$_m$—C$_{3-9}$ cycloalkyl optionally substituted by at least one substituent selected from a halogen, $C_{1-3}$-alkoxy, $C_{1-3}$-alkyl, $C_{1-3}$-haloalkoxy, $C_{1-3}$-haloalkyl, trihaloalkyl or a hydroxyl group; a —SO$_2$R$_5$ group; a —COR$_6$ group; a —CO$_2$R$_7$ group; or a —(C(R$_4$)$_2$)$_m$—CONR$_8$R$_9$;

$R_4$ is H or a $C_{1-6}$ alkyl;

$R_5$, $R_6$ and $R_7$ are a $C_{1-6}$ alkyl optionally substituted by at least one substituent selected from a halogen, $C_{1-3}$-alkoxy, $C_{1-3}$-alkyl, $C_{1-3}$-haloalkoxy, $C_{1-3}$-haloalkyl, trihaloalkyl or a hydroxyl group;

$R_8$ and $R_9$ independently represent a H, a $C_{1-6}$ alkyl; or a —(C(R$_4$)$_2$)$_m$-aryl, the aryl group being a 5 or 6-membered ring optionally substituted by at least one substituent selected from a 5 or 6-membered heterocycloalkyl, a halogen, $C_{1-3}$-alkoxy, $C_{1-3}$-alkyl, $C_{1-3}$-haloalkoxy, $C_{1-3}$-haloalkyl, trihaloalkyl or a hydroxyl group;

Z is CH$_2$ or C=O and n is 0 or, 1;

m is 0, 1 or 2;

or a pharmaceutically acceptable salt or isomer thereof.

2. A compound of claim 1 wherein $R_1$ is H; a $C_{1-6}$ alkyl optionally substituted by at least one substituent selected from a halogen, $C_{1-3}$-alkoxy, $C_{1-3}$-alkyl, $C_{1-3}$ haloalkoxy, $C_{1-3}$-haloalkyl, trihaloalkyl or a hydroxyl group; a 5 or 6-membered heterocycloalkyl having at least one heteroatom selected from O, N or S and being optionally substituted by at least one substituent selected from a halogen, $C_{1-3}$-alkoxy, $C_{1-3}$-alkyl, $C_{1-3}$-haloalkoxy, $C_{1-3}$-haloalkyl, trihaloalkyl or a hydroxyl group; a —(C(R$_4$)$_2$)$_m$—C$_{3-9}$ cycloalkyl, the cycloalkyl group being optionally substituted by at least one substituent selected from a halogen, $C_{1-3}$-alkoxy, $C_{1-3}$-alkyl, $C_{1-3}$-haloalkoxy, $C_{1-3}$-haloalkyl, trihaloalkyl or a hydroxyl group; or a —(C(R$_4$)$_2$)$_m$-aryl, the aryl group being a 5 or 6-membered ring optionally substituted by at least one substituent selected from a halogen, $C_{1-3}$-alkoxy, $C_{1-3}$-alkyl, $C_{1-3}$-haloalkoxy, $C_{1-3}$-haloalkyl, trihaloalkyl or a hydroxyl group.

3. A compound of claim 1, wherein $R_1$ is H, a $C_{1-6}$ alkyl or a group selected from:

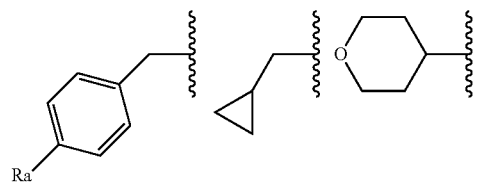

-continued

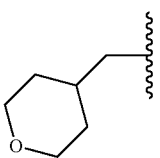

wherein $R_a$ represents a hydrogen, a halogen, $C_{1-3}$ alkyl, or a trihaloalkyl.

4. A compound of claim 1, wherein $R_2$ is a phenyl optionally substituted by at least one halogen atom.

5. A compound of claim 1, wherein $R_3$ is a H; a $C_{1-6}$ alkyl; —$(C(R_4)_2)_m$—$C_{3-9}$ cycloalkyl; a —$SO_2R_5$ group; a —$COR_6$ group; or a —$CO_2R_7$ group; wherein $R_5$, $R_6$ and $R_7$ are $C_{1-6}$ alkyl.

6. A compound of claim 1, wherein $R_1$ is H, a $C_{1-6}$ alkyl or a group selected from:

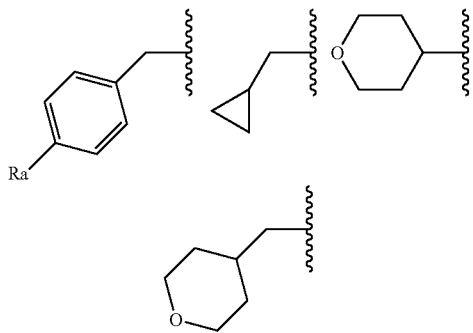

wherein $R_a$ represents a hydrogen, a halogen, $C_{1-3}$ alkyl, or a trihaloalkyl;

$R_2$ is a phenyl optionally substituted by at least one halogen atom; and $R_3$ is a H; a $C_{1-6}$ alkyl; —$(C(R_4)_2)_m$—$C_{3-9}$ cycloalkyl; a —$SO_2R_5$ group; a —$COR_6$ group; or a —$CO_2R_7$ group; wherein $R_5$, $R_6$ and $R_7$ are $C_{1-5}$ alkyl.

7. A compound of claim 1, having the following formula:

(Ie)
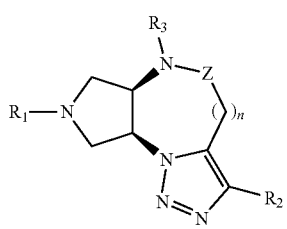

(If)
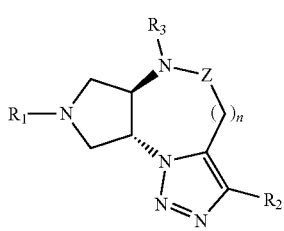

(Ig)
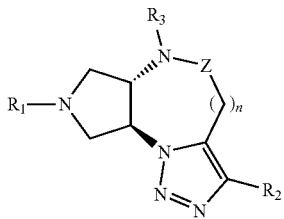

(Ih)
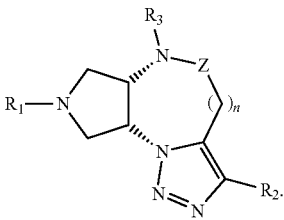

8. A compound of claim 1, selected from the group consisting of:
(rac) (5a,8a-trans)-7-benzyl-3-phenyl-5,5a,6,7,8,8a-hexahydro-4H-pyrrolo[3,4-e][1,2,3]triazolo[1,5-a]pyrazine, hydrochloride,
(rac)-(5a,8a-cis)-7-benzyl-3-phenyl-5,5a,6,7,8,8a-hexahydro-4H-pyrrolo[3,4-e][1,2,3]triazolo[1,5-a]pyrazin-4-one,
(rac) (5a,8a-cis)-7-benzyl-3-phenyl-5,5a,6,7,8,8a-hexahydro-4H-pyrrolo[3,4-e][1,2,3]triazolo[1,5-a]pyrazine,
(rac) 1-((5a,8a-trans)-7-benzyl-3-phenyl-6,7,8,8a-tetrahydro-4H-pyrrolo[3,4-e][1,2,3]triazolo[1,5-a]pyrazin-5(5aH)-yl)ethanone hydrochloride,
(rac)-(5a,8a-cis)-7-benzyl-3-phenyl-5-propyl-5,5a,6,7,8,8a-hexahydro-4H-pyrrolo[3,4-e][1,2,3]triazolo[1,5-a]pyrazin-4-one,
(rac)-(5a,8a-trans)-tert-butyl-3-phenyl-6,7,8,8a-tetrahydro-4H-pyrrolo[3,4-e][1,2,3]triazolo[1,5-a]pyrazine-5(5aH)-carboxylate,
(rac)-(5a,8a-trans)-tert-butyl-7-(4-fluorobenzyl)-3-phenyl-6,7,8,8a-tetrahydro-4H-pyrrolo[3,4-e][1,2,3]triazolo[1,5-a]pyrazine-5(5aH)-carboxylate, pq,66
(rac) (5a,8a-trans)-7-(4-fluorobenzyl)-3-phenyl-5,5a,6,7,8,8a-hexahydro-4H-pyrrolo[3,4-e][1,2,3]triazolo[1,5-a]pyrazine hydrochloride,
(rac) (5a,8a-trans)-7-benzyl-3-phenyl-5-propyl-5,5a,6,7,8,8a-hexahydro-4H-pyrrolo[3,4-e][1,2,3]triazolo[1,5-a]pyrazine hydrochloride,
(rac) (5a,8a-trans)-3-phenyl-5-propyl-5,5a,6,7,8,8a-hexahydro-4H-pyrrolo[3,4-e][1,2,3]triazolo[1,5-a]pyrazine hydrochloride,
(rac) (5a,8a-trans)-7-pentyl-3-phenyl-5-propyl-5,5a,6,7,8,8a-hexahydro-4H-pyrrolo[3,4-e][1,2,3]triazolo[1,5-a]pyrazine hydrochloride,
(rac) (5a,8a-cis)-7-benzyl-5-methyl-3-phenyl-5,5a,6,7,8,8a-hexahydro-4H-pyrrolo[3,4-e][1,2,3]triazolo[1,5-a]pyrazine,
(rac) (5a,8a-cis)-7-benzyl-3-phenyl-5-propyl-5,5a,6,7,8,8a-hexahydro-4H-pyrrolo[3,4-e][1,2,3]triazolo[1,5-a]pyrazine,
(rac) (5a,8a-cis)-7-pentyl-3-phenyl-5,5a,6,7,8,8a-hexahydro-4H-pyrrolo[3,4-e][1,2,3]triazolo[1,5-a]pyrazine,
(5aS,8aR)-7-benzyl-3-phenyl-5,5a,6,7,8,8a-hexahydro-4H-pyrrolo[3,4-e][1,2,3]triazolo[1,5-a]pyrazine,
(rac) (5a,8a-trans)-7-benzyl-5-methyl-3-phenyl-5,5a,6,7,8,8a-hexahydro-4H-pyrrolo[3,4-e][1,2,3]triazolo[1,5-a]pyrazine hydrochloride, (rac) 1-((5a,8a-trans)-7-benzyl-3-phenyl-6,7,8,8a-tetra-hydro-4H-pyrrolo[3,4-e][1,2,3]triazolo[1,5-a]pyrazin-5(5aH)-yl)propan-1-one hydrochloride,
(rac) (5a,8a-trans)-7-(cyclopropyl-methyl)-3-phenyl-5,5a,6,7,8,8a-hexahydro-4H-pyrrolo[3,4-e][1,2,3]triazolo[1,5-a]pyrazine hydrochloride,
(rac) (5a,8a-trans)-3-phenyl-7-(tetrahydro-2H-pyran-4-yl)-5,5a,6,7,8,8a-hexahydro-4H-pyrrolo[3,4-e][1,2,3]triazolo[1,5-a]pyrazine hydrochloride,
(rac) (5a,8a-trans)-7-benzyl-5-(methylsulfonyl)-3-phenyl-5,5a,6,7,8,8a-hexahydro-4H-pyrrolo[3,4-e][1,2,3]triazolo[1,5-a]pyrazine hydrochloride,
(5aS,8aS)-7-benzyl-3-phenyl-5,5a,6,7,8,8a-hexahydro-4H-pyrrolo[3,4-e][1,2,3]triazolo[1,5-a]pyrazine hydrochloride,
(5aR,8aR)-7-benzyl-3-phenyl-5,5a,6,7,8,8a-hexahydro-4H-pyrrolo[3,4-e][1,2,3]triazolo[1,5-a]pyrazine hydrochloride,
(5aS,8aS)-7-(4-fluorobenzyl)-3-phenyl-5,5a,6,7,8,8a-hexahydro-4H-pyrrolo[3,4-e][1,2,3]triazolo[1,5-a]pyrazine hydrochloride,
(5aR,8aR)-7-(4-fluorobenzyl)-3-phenyl-5,5a,6,7,8,8a-hexahydro-4H-pyrrolo[3,4-e][1,2,3]triazolo[1,5-a]pyrazine hydrochloride,
(5aR,8aR)-7-(4-chlorobenzyl)-3-phenyl-5,5a,6,7,8,8a-hexahydro-4H-pyrrolo[3,4-e][1,2,3]triazolo[1,5-a]pyrazine hydrochloride,
(5aR,8aR)-3-phenyl-7-(4-(trifluoromethyl)benzyl)-5,5a,6,7,8,8a-hexahydro-4H-pyrrolo[3,4-e][1,2,3]triazolo[1,5-a]pyrazine hydrochloride,
(5aR,8aR)-3-phenyl-7-((tetrahydro-2H-pyran-4-yl)methyl)-5,5a,6,7,8,8a-hexahydro-4H-pyrrolo[3,4-e][1,2,3]triazolo[1,5-a]pyrazine hydrochloride,
(rac) (5a,8a-trans)-7-benzyl-3-(2-fluorophenyl)-5,5a,6,7,8,8a-hexahydro-4H-pyrrolo[3,4-e][1,2,3]triazolo[1,5-a]pyrazine hydrochloride,
(5aR,8aR)-7-benzyl-3-(2-fluorophenyl)-5,5a,6,7,8,8a-hexahydro-4H-pyrrolo[3,4-e][1,2,3]triazolo[1,5-a]pyrazine hydrochloride,
(rac) (6a,9a-cis)-8-benzyl-3-phenyl-4,5,6,6a,7,8,9,9a-octahydropyrrolo[3,4-b][1,2,3]triazolo[1,5-d][1,4]diazepine hydrochloride,
(rac) (6a,9a-cis)-8-benzyl-3-phenyl-6-propyl-4,5,6,6a,7,8,9,9a-octahydropyrrolo[3,4-b][1,2,3]triazolo[1,5-d][1,4]diazepine hydrochloride,
(rac) (6a,9a-cis)-8-benzyl-6-(cyclopropylmethyl)-3-phenyl-4,5,6,6a,7,8,9,9a-octahydropyrrolo[3,4-b][1,2,3]triazolo[1,5-d][1,4]diazepine hydrochloride,
(rac) 1-((6a,9a-cis)-8-benzyl-3-phenyl-4,5,7,8,9,9a-hexahydropyrrolo[3,4-b][1,2,3]triazolo[1,5-d][1,4]diazepin-6(6aH)-yl)propan-1-one hydrochloride,
(6aR,9aS)-8-benzyl-3-phenyl-4,5,6,6a,7,8,9,9a-octahydropyrrolo[3,4-b][1,2,3]triazolo[1,5-d][1,4]diazepine hydrochloride,
(6aS,9aR)-8-benzyl-3-phenyl-4,5,6,6a,7,8,9,9a-octahydropyrrolo[3,4-b][1,2,3]triazolo [1,5-d][1,4]-diazepine hydrochloride,
(rac)-(5a,8a-cis)-3-phenyl-5,5a,6,7,8,8a-hexahydro-4H-pyrrolo[3,4-e][1,2,3]triazolo[1,5-a]pyrazin-4-one hydrochloride and
(rac)-(5a,8a-cis)-7-benzyl-5-methyl-3-phenyl-5,5a,6,7,8,8a-hexahydro-4H-pyrrolo[3,4-e][1,2,3]triazolo[1,5-a]pyrazin-4-one.

9. A method of treating a patient suffering from a sigma receptor mediated disease or condition selected from the group consisting of pain, anxiety, depression, schizophrenia, and stress, the method comprising administering to the patient in need of such a treatment a therapeutically effective amount of a compound of claim 1 or a pharmaceutically acceptable salt or isomer thereof.

10. The method of claim 9, wherein the condition is pain, which is selected from the group consisting of neuropathic pain, inflammatory pain, and pain conditions involving allodynia and/or hyperalgesia.

11. The method of claim 9, wherein the condition is selected from stress, cancer, depression, anxiety, and schizophrenia.

12. A process for the preparation of a compound of claim 1 which is of formula (I):

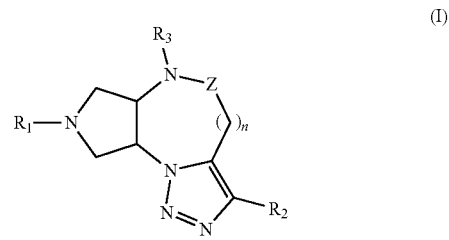

comprising the cycloaddition reaction in a non-polar solvent of a compound of formula (II):

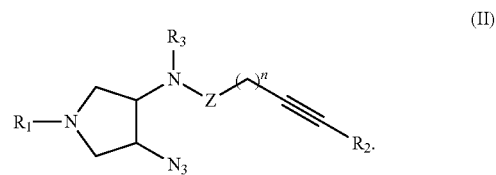

13. A process for the preparation of a compound of claim 1 which is of formula (I):

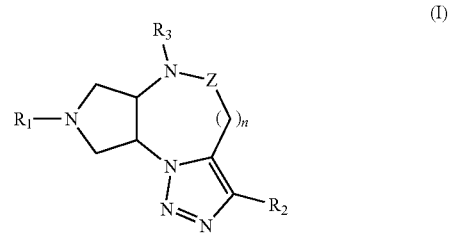

comprising the reaction in an organic solvent of a compound of formula (Ic):

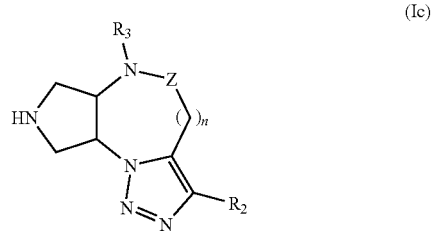

with a compound of general formula (IIIa) or (VIa):

-continued

(VIa)

wherein X is a suitable leaving group.

14. A process for the preparation of a compound of claim 1 which is of formula (I):

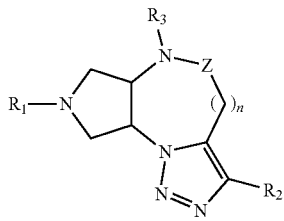

(I)

comprising the reaction in an organic solvent of a compound of formula (Id):

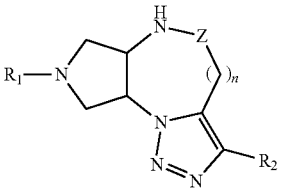

(Id)

with a compound of formula (IIIb), (IV), (V) or (VIb):

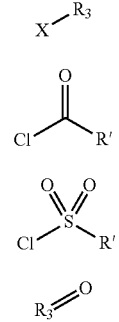

(IIIb)

(IVb)

(Vb)

(VIb)

wherein R' stands for $R_5$ and $R_6$ and X is a suitable leaving group.

15. A pharmaceutical composition comprising at least one compound of claim 1, or a pharmaceutically acceptable salts or isomers thereof, and at least a pharmaceutically acceptable carrier, additive, adjuvant or vehicle.

16. The process of claim 13, wherein X is halogen or sulfonate.

17. The process of claim 14, wherein X is halogen or sulfonate.

* * * * *

UNITED STATES PATENT AND TRADEMARK OFFICE
CERTIFICATE OF CORRECTION

PATENT NO.        : 10,035,805 B2
APPLICATION NO.   : 15/323228
DATED             : July 31, 2018
INVENTOR(S)       : Félix Cuevas-Cordobés and Miguel Angel Pericás-Brondo Page 1 of 1

It is certified that error appears in the above-identified patent and that said Letters Patent is hereby corrected as shown below:

In the Claims

Column 49, Line 39: Insert --$C_{1-3}$-alkyl,-- after "$C_{1-3}$-alkoxy".
    Line 42: Insert --$C_{1-3}$-alkyl,-- after "$C_{1-3}$-alkoxy" and delete "$C_{1-3}$-" at the end of the line.
    Line 43: Delete "haloalkoxy," at the beginning of the line.
    Line 47: insert --$C_{1-3}$-alkyl,-- after "$C_{1-3}$-alkoxy".

Column 51, Line 45: "$C_{1-5}$-alkyl" should read --$C_{1-6}$-alkyl--.

Column 52, Line 42: Delete "pq,66" at the end of the line.

Column 54, Line 9: Delete "cancer".
    Line 63: Delete "general".

Column 56, Line 23: "salts" should read --salt--.
    Line 24: "isomers" should read --isomer--.

Signed and Sealed this
Fourteenth Day of May, 2019

Andrei Iancu
*Director of the United States Patent and Trademark Office*